(12) United States Patent
Bang et al.

(10) Patent No.: US 12,115,212 B2
(45) Date of Patent: Oct. 15, 2024

(54) METHODS OF DECREASING AMYLOID BETA (Aβ) PLAQUE DEPOSITION AND HYPERPHOSPHORYLATED TAU PLAQUE DEPOSITION IN ALZHEIMER'S DISEASE USING A CYSTATIN C FUSION PROTEIN

(71) Applicant: L & J Bio Co., Ltd., Seoul (KR)

(72) Inventors: Sookhee Bang, Fairfax, VA (US); Jeong Kuen Song, Gaithersburg, MD (US); Seung-Wook Shin, Clarksburg, MD (US); Kwan Hee Lee, Las Vegas, NV (US); Ho June Lee, Potomac, MD (US)

(73) Assignee: L & J Bio Co., Ltd., Seoul (KR)

( * ) Notice: Subject to any disclaimer, the term of this patent is extended or adjusted under 35 U.S.C. 154(b) by 584 days.

(21) Appl. No.: 16/556,957

(22) Filed: Aug. 30, 2019

(65) Prior Publication Data

US 2020/0230218 A1    Jul. 23, 2020

Related U.S. Application Data

(60) Provisional application No. 62/794,147, filed on Jan. 18, 2019.

(51) Int. Cl.
| | | |
|---|---|---|
| *A61K 38/00* | (2006.01) | |
| *A61K 38/17* | (2006.01) | |
| *A61K 38/18* | (2006.01) | |
| *A61K 38/22* | (2006.01) | |
| *A61K 38/38* | (2006.01) | |
| *A61K 38/46* | (2006.01) | |
| *A61K 38/50* | (2006.01) | |
| *A61K 38/57* | (2006.01) | |
| *A61P 25/00* | (2006.01) | |
| *A61P 25/28* | (2006.01) | |
| *C07K 14/00* | (2006.01) | |
| *C07K 14/47* | (2006.01) | |

(52) U.S. Cl.
CPC .......... *A61K 38/57* (2013.01); *A61K 38/1709* (2013.01); *A61K 38/1774* (2013.01); *A61K 38/179* (2013.01); *A61K 38/385* (2013.01); *A61K 38/465* (2013.01); *A61K 38/50* (2013.01); *A61P 25/28* (2018.01)

(58) Field of Classification Search
CPC .......... A61P 25/28; A61P 25/16; A61P 25/00; C07K 2319/00; C07K 2319/33; C07K 14/47; C07K 14/00; C07K 14/4702; C07K 219/03; C07K 2319/31; C07K 2319/50; C07K 14/8139; A61K 38/00; A61K 38/385; A61K 38/57; A61K 38/1709; G01N 2333/4709
See application file for complete search history.

(56) References Cited

U.S. PATENT DOCUMENTS

| | | | | |
|---|---|---|---|---|
| 7,790,673 | B2 * | 9/2010 | Levy ................ | A61K 38/57 514/17.7 |
| 8,012,929 | B2 * | 9/2011 | Gazit ............... | C07K 5/1024 514/17.8 |
| 8,741,883 | B2 * | 6/2014 | Yang ................ | C07D 417/10 514/183 |
| 8,993,510 | B2 * | 3/2015 | Gazit ............... | C07K 5/0812 514/1.1 |
| 9,834,582 | B2 * | 12/2017 | Wisniewski ...... | A61P 25/28 |
| 10,905,770 | B2 * | 2/2021 | Roizman .......... | A61K 31/436 |
| 2006/0183800 | A1 * | 8/2006 | Kong ................ | C07C 309/14 562/105 |
| 2010/0232149 | A1 * | 9/2010 | Liao ................. | F21L 4/027 362/196 |
| 2010/0292149 | A1 * | 11/2010 | Bowser ............ | A61K 38/1709 514/10.9 |
| 2015/0320706 | A1 * | 11/2015 | Imbimbo .......... | C07K 16/18 424/178.1 |
| 2016/0136293 | A1 * | 5/2016 | Littman ............ | A61K 38/45 424/190.1 |
| 2017/0151339 | A1 * | 6/2017 | White ............... | A61P 35/00 |
| 2018/0009883 | A1 * | 1/2018 | Volker Corte-Real ............ A61P 43/00 | |
| 2018/0028679 | A1 * | 2/2018 | Kratz ............... | A61K 47/643 |
| 2018/0100158 | A1 * | 4/2018 | Del'Guidice ..... | C07K 16/18 |
| 2019/0015521 | A1 * | 1/2019 | Roizman .......... | A61P 29/00 |

FOREIGN PATENT DOCUMENTS

| | | | |
|---|---|---|---|
| CN | 105254763 | * | 1/2016 |
| EP | 3385285 A1 | | 10/2018 |

(Continued)

OTHER PUBLICATIONS

Falkenburger et al., J. Neural. Transm, 2006; 70:261-268.*
Tayebati, Mech. Ageing Dev. 2006. 127: 100-8.*
Sarter, Neurosci. and Biobehav. Rev. 2004. 28: 645-650.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*

(Continued)

*Primary Examiner* — Chang-Yu Wang
(74) *Attorney, Agent, or Firm* — FisherBroyles, LLP; Joseph Hyosuk Kim

(57) ABSTRACT

The present application discloses a method for treating a protein deficiency in the central nervous system of a subject in need thereof, comprising systemically administering to the subject a therapeutically effective dose of a fusion polypeptide comprising the first protein, wherein the fusion polypeptide comprises: (a) the first protein; (b) a second protein that provides extended circulation-lifetime in vivo and (c) blood brain barrier crossing facilitating peptide; wherein the fusion polypeptide crosses the blood brain barrier (BBB).

4 Claims, 18 Drawing Sheets

Specification includes a Sequence Listing.

(56) References Cited

FOREIGN PATENT DOCUMENTS

| WO | WO2015/023894 | * | 2/2015 |
| WO | WO2016/161516 | * | 10/2016 |

OTHER PUBLICATIONS

Guo et al., PNAS 2004; 101:9205-9210.*
Anger. Neurotoxicology 1991. 12: 403-13.*
Jagmag et al., Front. Neurosci. 2016; 9:503. Doi:10.3389/fnins. 2015.00503.*
Potashikin et al., Parkinson's Disease, 2011; 658083; doi:104061/2011/658083.*
Henstridge et al., Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Duan et al. Mol. Cell. Neurosci. 2018; 89:1-8.*
Mathews et al.,Ageing Res Rev. 2016; 32:38-50.*
Zhang et al.Bioconjug. Chem. 2013; 24:604-613. doi:10.1021/bc300585h.*
Bang et al. Neurosci. Lett. 2022; 767:136298.doi.org/10.1016/j.neulet.2021.136298.*
Kaur et al. Front. Mol. Neurosci. 2012; 5:articel 9. doi:10.3380/fnmol.2012.00079.*
CN105254763—English translated version, published Jan. 20, 2016.*
Hurtado et al., Am.J. Pathol. 2010; 177:1977-1988.*
Hardie, D.G. , "AMP-activated Protein Kinase: an Enrgy Sensor That Regulates All Aspects of Cell Function," Genes and Development 25(18):1895-1908, Cold Spring Harbor Laboratory Press, United States (Sep. 2011).
Hardy, J. and Selkoe, D.J., "The Amyloid Hypothesis of Alzheimer's Disease: Progress and Problems on the Road to Therapeutics," Science 297(5580):353-356, American Association for the Advancement of Science, United States (Jul. 2002).
Hardy, J.A. and Higgins, G.A. , "Alzheimer's Disease: the Amyloid Cascade Hypothesis," Science 256(5054):184-185, American Association for the Advancement of Science, United States (Apr. 1992).
Hensley, K., et al., "A Model for Beta Amyloid Aggregation and Neurotoxicity Based on Free Radical Generation by the Peptide: Relevance to Alzheimer Disease," Proceedings of the National Academy of Sciences of the United States of America 91(18):3270-3274 (Apr. 1994).
Hsiao, K., et al., "Correlative Memory Deficits, Abeta Elevation, and Amyloid Plaques in Transgenic Mice," Science 274(5284):99-102, American Association for the Advancement of Science, United States (Oct. 1996).
Hyman, B.T., et al., "Alzheimer's Disease: Cell-specific Pathology Isolates the Hippocampal Formation," Science 225(4667):1168-1170, American Association for the Advancement of Science, United States (Sep. 1984).
Hyman, B.T., et al., "Perforant Pathway Changes and the Memory Impairment of Alzheimer's Disease," Annals of Neurology 20(4):472-481, Wiley-Liss, United States (Oct. 1986).
Ishihara, T., et al., "Age-dependent Emergence and Progression of a Tauopathy in Transgenic Mice Overexpressing the Shortest Human Tau Isoform," Neuron 24(3):751-762, Cell Press, United States (Nov. 1999).
Jumblatt, J.E. and Tischler, A.S., "Regulation of Muscarinic Ligand Binding Sites by Nerve Growth Factor in Pc12 Phaeochromocytoma Cells," Nature 297(5862):152-154, Nature Publishing Group, England (May 1982).
Juszczyk, P., et al., "Binding Epitopes and Interaction Structure of the Neuroprotective Protease Inhibitor Cystatin C With B-amyloid Revealed by Proteolytic Excision Mass Spectrometry and Molecular Docking Simulation," Journal of Medicinal Chemistry 52(8):2420-2428, American Chemical Society, United States (Apr. 2009).
Kang, Y.S., et al., "Donepezil, Tacrine and Alpha-phenyl-n-tert-butyl Nitrone (Pbn) Inhibit Choline Transport by Conditionally Immortalized Rat Brain Capillary Endothelial Cell Lines (Tr-bbb)," Archives of Pharmacal Research 28(4):443-450, Pharmaceutical Society of Korea (Apr. 2005).
Kilic, E., et al., "Intravenous Tat-bcl-xl is Protective After Middle Cerebral Artery Occlusion in Mice," Annals of Neurology 52(5):617-622, Wiley-Liss, United States (Nov. 2002).
Kim, J., et al., "AMPK and mTOR Regulate Autophagy Through Direct Phosphorylation of Ulk1," Nature Cell Biology 13:132-141 ( Jan. 2011).
Kim, M.H., et al., "Evidence of Carrier-mediated Transport in the Penetration of Donepezil Into the Rat Brain," Journal of Pharmaceutical Sciences 99(3):1548-1566, Elsevier, United States (Mar. 2010).
Knowles, R.B., et al., "Abeta Associated Neuropil Changes: Correlation With Neuronal Loss and Dementia," Journal of Neuropathology and Experimental Neurology 57(12):1122-1130, Oxford University Press, England ( Dec. 1998).
Kosik, K.S., et al., "Microtubule-associated Protein Tau (Tau) is a Major Antigenic Component of Paired Helical Filaments in Alzheimer Disease," Proceedings of the National Academy of Sciences of the United States of America 83(11):4044-4048, National Academy of Sciences, United States (Jun. 1986).
Ksiezak-Reding H., et al., "Phosphate Analysis and Dephosphorylation of Modified Tau Associated With Paired Helical Filaments," Brain Research 597(2):209-219, North-Holland Biomedical Press, Netherlands ( Dec. 1992).
Lace, G., et al., "Hippocampal Tau Pathology is Related to Neuroanatomical Connections: an Ageing Population- based Study," Brain 132(Pt5):1324-1334, Oxford University Press, England (May 2009).
Lauritzen, I., et al., "The β-secretase Derived C-terminal Fragment of βAPP, C99, but not Aβ, is a Key Contributor to Early Intraneuronal Lesions in Triple Transgenic Mouse Hippocampus," The Journal of Neuroscience 32(46):16243-1655a, Society for Neuroscience, United States (Nov. 2012).
Lee, V.M., et al., "A68: a Major Subunit of Paired Helical Filaments and Derivatized Forms of Normal Tau," Science 251(4994):675-678, American Association for the Advancement of Science, United States (Feb. 1991).
Lee, V.M., et al., "Neurodegenerative Tauopathies," Annual Review of Neuroscience 24:1121-1159, Annual Review of Neuroscience (2001).
Lewis, J., et al., "Neurofibrillary Tangles, Amyotrophy and Progressive Motor Disturbance in Mice Expressing Mutant (P301I) Tau Protein," Nature genetics 25(4):402-405, Nature Pub. Co., United States (Aug. 2000).
Li, M., et al., "The myeloid leukemia-associated protein SET is a potent inhibitor of protein phosphatase 2A," The Journal of Biological Chemistry 271(19): 11059-11062, American Society for Biochemistry and Molecular Biology, United States (May 1996).
Liao, M.C., et al., "Degradation of Amyloid beta Protein by Purified Myelin Basic Protein," The Journal of Biological Chemistry 284:28917-28925, American Society for Biochemistry and Molecular Biology, United States (Oct. 2009).
Lim, S., et al., "dNP2 is a Blood-brain Barrier-permeable Peptide Enabling ctCTLA-4 Protein Delivery to Ameliorate Experimental Autoimmune Encephalomyelitis," Nature Communications 6:8244, Nature Pub. Group, England (Sep. 2015).
Lin, W.L., et al., "Ultrastructural Neuronal Pathology in Transgenic Mice Expressing Mutant (P301I) Human Tau," Journal of Neurocytology 32(9):1091-1105, Kluwer Academic Publishers, United States ( Nov. 2003).
Lin, Y.T., et al., "The Binding and Phosphorylation of Thr231 is Critical for Tau's Hyperphosphorylation and Functional Regulation by Glycogen Synthase Kinase 3B," Journal of Neurochemistry 103(2):802-813, Oxford, England (Oct. 2007).
Liu, F., et al., "Contributions of Protein Phosphatases PP1, PP2A, PP2B and PP5 to the Regulation of Tau Phosphorylation," The European Journal of Neuroscience 22(8):1942-1950, Wiley-Blackwell, France ( Oct. 2005).
Malakoutikhah, M., et al., "Shuttle-mediated Drug Delivery to the Brain," Angewandte Chemie (International ed. in English) 50(35): 7998-8014, Wiley-VCH, Germany (Aug. 2011).
Manfredini, S., et al., "Design, Synthesis and Activity of Ascorbic Acid Prodrugs of Nipecotic, Kynurenic and Diclophenamic Acids,

(56) References Cited

OTHER PUBLICATIONS

Liable to Increase Neurotropic Activity," Journal of Medicinal Chemistry 45(3): 559-562, American Chemical Society, United States (Jan. 2002).
Medina, M. and Avila, J., "Further Understanding of Tau Phosphorylation: Implications for Therapy," Expert Review of Neurotherapeutics 15(1):115-122, Taylor & Francis, England (Jan. 2015).
Nakagawa, S., et al., "A New Blood-brain Barrier Model Using Primary Rat Brain Endothelial Cells, Pericytes and Astrocytes," Neurochemistry International 54(3-4): 253-263, Pergamon Press, England (Ma.-Apr. 2009).
Nakamura, Y., et al., "Immunohistochemical Localization of Ca(2+)/calmodulin-dependent Protein Kinase Kinase Beta in the Rat Central Nervous System," Neuroscience Research 39(2):175-188 (Feb. 2001).
Neddens, J., et al., "Phosphorylation of Different Tau Sites During Progression of Alzheimer's Disease," Acta Neuropathologica Communications 6(1):52, BioMed Central, England (Jun. 2018).
Ng, S.K., "Generation of High-expressing Cells by Methotrexate Amplification of Destabilized Dihydrofolate Reductase Selection Marker," Methods in Molecular Biology 801:161-172, Humana Press, United States (2012).
Patabendige, A., et al., "A Detailed Method for Preparation of a Functional and Flexible Blood-brain Barrier Model Using Porcine Brain Endothelial Cells," Brain Research 1521:16-30, North-Holland Biomedical Press, Netherlands (Jul. 2013).
Prades, R., et al., "Applying the Retro-enantio Approach to Obtain a Peptide Capable of Overcoming the Blood-brain Barrier," Angewandte Chemie (International ed. in English) 54(13):3967-3972, Academic Press, Germany (Mar. 2015).
Reilly, J.F., et al., "Amyloid Deposition in the Hippocampus and Entorhinal Cortex: Quantitative Analysis of a Transgenic Mouse Model," Proceedings of the National Academy of Sciences of the United States of America 100(8):4837-4842, National Academy of Sciences, United States (Apr. 2003).
Reiman, E.M., "Alzheimer's Disease: Attack on Amyloid-B Protein," Nature 537(7618):36-37, Nature Publishing Group, England (Sep. 2016).
Rosenmann, H., "Asparagine Endopeptidase Cleaves Tau and Promotes Neurodegeneration," Nature Medicine 20(11):1236-1238, Nature Publishing Company, United States (Nov. 2014).
Rub, U., et al., "The Evolution of Alzheimer's Disease-related Cytoskeletal Pathology in the Human Raphe Nuclei," Neuropathology and Applied Neurobiology 26(6):553-567, Blackwell Scientific Publications, England (Dec. 2000).
Sagare, A.P., et al., "A Lipoprotein Receptor Cluster Iv Mutant Preferentially Binds Amyloid-B and Regulates Its Clearance From the Mouse Brain," The Journal of Biological Chemistry 288(21):15154-15166, American Society for Biochemistry and Molecular Biology, United States (May 2013).
Salminen, A., et al., "AMP-activated Protein Kinase: a Potential Player in Alzheimer's Disease," Journal of Neurochemistry 118(4):460-474, Wiley on behalf of the International Society for Neurochemistry, England (Aug. 2011).
Sand, K.M., et al., "Unraveling the Interaction Between Fcrn and Albumin: Opportunities for Design of Albumin-based Therapeutics," Frontiers in Immunology 5(682): 1-21, Frontiers Research Foundation, Switzerland (Jan. 2015).
Sassin, I., et al., "Evolution of Alzheimer's Disease-related Cytoskeletal Changes in the Basal Nucleus of Meynert," Acta Neuropathologica 100(3):259-69, Springer Verlag, Germany (Sep. 2000).
Selenica, M.L., et al., "Cystatin C Reduces the in Vitro Formation of Soluble aß1-42 Oligomers and Protofibrils," Scandinavian Journal of Clinical and Laboratory Investigation 67(2):179-190, Informa Healthcare, England (2007).
Sengupta, A., et al., "Phosphorylation of Tau at both Thr 231 and Ser 262 is required for Maximal Inhibition of its Binding to Microtubules," Archives of Biochemistry and Biophysics 357(2):299-309, Academic Press, United States (Sep. 1998).

Seubert, P., et al., "Detection of Phosphorylated Ser262 in Fetal Tau, Adult Tau, and Paired Helical Filament Tau," The Journal of Biological Chemistry 270(32):18917-18922, American Society for Biochemistry and Molecular Biology, United States (Aug. 1995).
Sevigny, J., et al., "The Antibody Aducanumab Reduces aß Plaques in Alzheimer's Disease," Nature 537(7618):50-56, Nature Publishing Group, England (Sep. 2016).
Spillantini, M.G., et al., "Tau Pathology and Neurodegeneration," The Lancet Neurology 12(6):609-22, Lancet Pub Group, England (Jun. 2013).
Steinberg, G.R., et al., "Ampk in Health and Disease," Physiological Reviews 89(3):1025-78, American Physiological Society, United States (Jul. 2009).
Su Y., et al., "Selective Deposition of Amyloid-b Protein in the Entorhinal-dentate Projection of a Transgenic Mouse Model of Alzheimer's Disease," Journal of Neuroscience Research 53(2):177-186, Wiley Interscience, United States (Jul. 1998).
Sundelof, J., et al., "Serum Cystatin C and the Risk of Alzheimer Disease in Elderly Men," Neurology 71(14):1072-1079, Lippincott Williams & Wilkins, United States (Sep. 2008).
Tan, J., et al., "Bcl-x(L) Inhibits Apoptosis and Necrosis Produced by Alzheimer's Beta-amyloid1-40 Peptide in Pc12 Cells," Neuroscience Letters 272(1):5-8, Elsevier Scientific Publishers, Ireland (Sep. 1999).
Thornton, C., et al., "Amp-activated Protein Kinase (Ampk) is a Tau Kinase, Activated in Response to Amyloid B-peptide Exposure," The Biochemical Journal 434(3):503-512, Portland Press, England (Mar. 2011).
Tizon, B., et al., "Cystatin C Protects Neuronal Cells From Amyloid-beta-induced Toxicity," Journal of Alzheimer's Disease 19(3):885-94, IOS Press, Netherland (2010).
Toschi, E., et al., "Activation of Matrix-metalloproteinase-2 and Membrane-type-1-matrix-metalloproteinase in Endothelial Cells and Induction of Vascular Permeability in Vivo by Human Immunodeficiency Virus-1 Tat Protein and Basic Fibroblast Growth Factor," Molecular Biology of the Cell 12(10):2934-2946, American Society for Cell Biology, United States (Oct. 2001).
Trojanowski, J.Q., et al., "Distribution of Tau Proteins in the Normal Human Central and Peripheral Nervous System," The Journal of Histochemistry and Cytochemistry 37(2):209-215, SAGE Publications, United States (Feb. 1989).
Tulving, E., et al., "Episodic and Declarative Memory: Role of the Hippocampus," Hippocampus 8(3):198-204, Wiley, United States (1998).
Van Kasteren, S.I., et al., "A Multifunctional Protease Inhibitor to Regulate Endolysosomal Function," Acs Chemical Biology 6(11):1198-1204, American Chemical Society, United States (Nov. 2011).
Van Strien, N.M., et al., "The Anatomy of Memory: an Interactive Overview of the Parahippocampal-hippocampal Network," Nature Reviews Neuroscience 10(4):272-282, Nature Pub Group, England (Apr. 2009).
Vingtdeux, V., et al., "Ampk is Abnormally Activated in Tangle- and Pre-tangle-bearing Neurons in Alzheimer's Disease and Other Tauopathies," Acta Neuropathologica 121(3):337-49, Springer Verlag, Germany (Mar. 11).
Vitale, F., et al., "Anti-tau Conformational Scfv Mc1 Antibody Efficiently Reduces Pathological Tau Species in Adult Jnpl3 Mice," Acta Neuropathologica Communications 6(1):82, BioMed Central, England (Aug. 2018).
Walsh, D.M., et al., "Alzheimer's Disease and the Amyloid Beta-protein," Progress in Molecular Biology and Translational Science 107:101-124, Elsevier, Netherland (2012).
Wang, J.Z., et al., "Abnormal Hyperphosphorylation of Tau: Sites, Regulation, and Molecular Mechanism of Neurofibrillary Degeneration," Journal of Alzheimer's Disease 33(Suppl1):S123-139, IOS Press, Netherland (2013).
Wang, J.Z., et al., "Kinases and Phosphatases and Tau Sites Involved in Alzheimer Neurofibrillary Degeneration," The European Journal of Neuroscience 25(1):59-68, Oxford University Press, France (Jan. 2007).
Wang, N., et al., "Construction of Biomimetic Long-circulation Delivery Platform Encapsulated by Zwitterionic Polymers for Enhanced

(56) References Cited

OTHER PUBLICATIONS

Penetration of Blood-brain Barrier," Rsc Advances 7(34):20766-20778, Royal soceity of chemistry (Apr. 2017).

Xu, R., et al., "Hiv-1 Tat Protein Increases the Permeability of Brain Endothelial Cells by Both Inhibiting Occludin Expression and Cleaving Occludin via Matrix Metalloproteinase-9," Brain Research 1436:13-19, Elsevier, Netherland (Feb. 2012).

Xu, W., et al., "Early Hyperactivity in Lateral Entorhinal Cortex is Associated With Elevated Levels of aβpp Metabolites in the Tg2576 Mouse Model of Alzheimer's Disease," Experimental Neurology 264:82-91, Academic Press, United States (Feb. 2015).

Zhang, X., et al., "Peptides in Cancer Nanomedicine: Drug Carriers, Targeting Ligands and Protease Substrates," Journal of Controlled Release 159(1):2-13, Elsevier, Netherland (Apr. 2012).

Zhang, X., et al., "Tumor-suppressor Pten Affects Tau Phosphorylation, Aggregation, and Binding to Microtubules," Faseb Journal 20(8):1272-4, The Federation, United States (Jun. 2006).

Zhao, J., et al., "Effects of Pten Inhibition on the Regulation of Tau Phosphorylation in Rat Cortical Neuronal Injury After Oxygen and Glucose Deprivation," Brain Injury 30(9):1150-1159, Informa Healthcare, England (2016).

Zhong, Y., et al., "Hiv-1 Tat Triggers Nuclear Localization of Zo-1 via Rho Signaling and Camp Response Element-binding Protein Activation," The Journal of Neuroscience 32(1):143-150, Society for Neuroscience, United States (Jan. 2012).

Zong, H., et al., "Homodimerization is Essential for the Receptor for Advanced Glycation End Products (Rage)-mediated Signal Transduction," The Journal of Biological Chemistry 285(30):23137-23146, American Society for Biochemistry and Molecular Biology, United States (Jul. 2010).

Mathews, Paul M., et al., "Cystatin C in aging and in Alzheimer's disease," Ageing Res Rev., vol. 32, Dec. 2016, pp. 38-50.

Wang, Meizhu, et al., "TAT-HSA-α-MSH fusion protein with extended half-life inhibits tumor necrosis factor-α in brain inflammation of mice," Appl Microbiol Biotechnol, vol. 100, 2016, pp. 5353-5361.

International Search Report and Written Opinion of the International Searching Authority mailed Jun. 5, 2020, issued in International Application No. PCT/US2020/014338, 28 pages.

Acker, C.M., et al., "Sensitive Quantitative Assays for Tau and Phospho-tau in Transgenic Mouse Models," Neurobiology of Aging 34(1):338-350, Elsevier, United States (Jan. 2013).

Alvarez-Fernandez, M., et al., "Inhibition of Mammalian Legumain by Some Cystatins is Due to a Novel Second Reactive Site," The Journal of Biological Chemistry 274(27):19195-19203, American Society for Biochemistry and Molecular Biology, United States (Jul. 1999).

Alvarez, P., et al., "Damage Limited to the Hippocampal Region Produces Long-lasting Memory Impairment in Monkeys," The Journal of Neuroscience 15(5):3796-807, Society for Neuroscience, United States (May 1995).

Amy, C.M., et al., "Increased Sodium Ion Conductance Through Nicotinic Acetylcholine Receptor Channels in Pc12 Cells Exposed to Nerve Growth Factors," The Journal of Neuroscience 3(8):1547-1553, Society for Neuroscience, United States (Aug. 1983).

Anderson, J.T., et al., "Extending Serum Half-life of Albumin by Engineering Neonatal Fc Receptor (Fcrn) Binding," The Journal of Biological Chemistry 289(19):13492-13502, American Society for Biochemistry and Molecular Biology, United States (Mar. 2014).

Andras, I.E., et al., "Signaling Mechanisms of Hiv-1 Tat-induced Alterations of Claudin-5 Expression in Brain Endothelial Cells," Journal of Cerebral Blood Flow and Metabolism 25(9):1159-1170, SAGE Publications, United kingdom (Sep. 2005).

Arnaud, L., et al., "Mechanism of Inhibition of Pp2a Activity and Abnormal Hyperphosphorylation of Tau by I2pp2a/set," Febs Letters 585(17):2653-2659, John Wiley & Sons Ltd, England (Jul. 2011).

Arriagada, P.V., et al., "Neurofibrillary Tangles but Not Senile Plaques Parallel Duration and Severity of Alzheimer's Disease," Neurology 42(3):631-9, Lippincott Williams & Wilkins, United States (Mar. 1992).

Augustinack, J.C., et al., "Specific Tau Phosphorylation Sites Correlate With Severity of Neuronal Cytopathology in Alzheimer's Disease," Acta Neuropathologica 103(1):26-35, Springer Verlag, Germany (Jan. 2002).

Ballatore, C., et al., "Tau-mediated Neurodegeneration in Alzheimer's Disease and Related Disorders," Nature Reviews Neuroscience 8(9):663-672, Nature Pub Group, United kingdom (Sep. 2007).

Bang, S., et al., "Amp-activated Protein Kinase is Physiologically Regulated by Inositol Polyphosphate Multikinase," Proceedings of the National Academy of Sciences of the United States of America 109(2):616-620, National Academy of Sciences, United States (Jan. 2012).

Bang, S., et al., "Convergence of Ipmk and Lkb1-ampk Signaling Pathways on Metformin Action," Molecular Endocrinology 28(7):1186-1193, Endocrine Society, United States (Jul. 2014).

Banks, W.A., et al., "Drug Delivery to the Brain in Alzheimer's Disease: Consideration of the Blood-brain Barrier," Advanced Drug Delivery Reviews 64(7):629-639, Elsevier Science Publishers, Netherland (May 2012).

Banks, W.A., et al., "From Blood-brain Barrier to Blood-brain Interface: New Opportunities for Cns Drug Delivery," Nature Reviews Drug Discovery 15(4):275-292, Nature Pub Group, United kingdom (Apr. 2016).

Banks, W.A., et al., "Permeability of the Blood-brain Barrier to Hiv-1 Tat," Experimental Neurology 193(1):218-227, Academic Press, United States (May 2005).

Bannerman, D.M., et al., "The Role of the Entorhinal Cortex in Two Forms of Spatial Learning and Memory," Experimental Brain Research 141(3):281-303, Springer Verlag, Germany (Dec. 2001).

Basurto-Islas, G., et al., "Activation of Asparaginyl Endopeptidase Leads to Tau Hyperphosphorylation in Alzheimer Disease," The Journal of Biological Chemistry 288(24):17495-17507, American Society for Biochemistry and Molecular Biology, United States (Jun. 2013).

Boado, R.J., et al., "Blood-brain Barrier Molecular Trojan Horse Enables Imaging of Brain Uptake of Radioiodinated Recombinant Protein in the Rhesus Monkey," Bioconjugate Chemistry 24(10):1741-9, American Chemical Society, United States (Oct. 2013).

Boado, R.J., et al., "Fusion Antibody for Alzheimer's Disease With Bidirectional Transport Across the Blood-brain Barrier and Abeta Fibril Disaggregation," Bioconjugate Chemistry 18(2):447-455, American Chemical Society, United States (Mar. 2007).

Boado, R.J., et al., "Genetic Engineering of a Lysosomal Enzyme Fusion Protein for Targeted Delivery Across the Human Blood-brain Barrier," Biotechnology and Bioengineering 99(2):475-484, Hoboken, United States (Feb. 2008).

Boado, R.J., et al., "Pharmacokinetics and Brain Uptake of a Genetically Engineered Bifunctional Fusion Antibody Targeting the Mouse Transferrin Receptor," Molecular Pharmaceutics 7(1):237-244, American Chemical Society, United States (Sep. 2009).

Braak, H., et al., "Diagnostic Criteria for Neuropathologic Assessment of Alzheimer's Disease," Neurobiology of Aging 18(4):S85-8, Elsevier, United States (Jul. 1997).

Braak, H., et al., "Neuropathological Stageing of Alzheimer-related Changes," Acta Neuropathologica 82(4):239-259, Springer Verlag, Germany (1991).

Braak, H., et al., "Staging of Alzheimer's Disease-related Neurofibrillary Changes," Neurobiology of Aging 16(3):271-284, Elsevier, United States (May 1995).

Braak, H., et al., "Vulnerability of Cortical Neurons to Alzheimer's and Parkinsons's Diseases," Journal of Alzheimer's Disease 9(3):35-44, IOS Press, Netherland (2006).

Bramblett, G.T., et al., "Abnormal Tau Phosphorylation at Ser396 in Alzheimer's Disease Recapitulates Development and Contributes to Reduced Microtubule Binding," Neuron 10(6):1089-1099, Cell Press, United States (Jun. 1993).

Brandt, R., et al., "Interaction of Tau With the Neural Plasma Membrane Mediated by Tau's Amino-terminal Projection Domain,"

(56) References Cited

OTHER PUBLICATIONS

The Journal of Cell Biology 131(5):1327-1340, Rockefeller University Press, United States (Dec. 1995).
Brewster, M.E., et al., "Evaluation of a Brain-targeting Zidovudine Chemical Delivery System in Dogs," Antimicrobial Agents and Chemotherapy 41(1):122-128, American Society for Microbiology, United States (Jan. 1997).
Buckmaster, C.A., et al., "Entorhinal Cortex Lesions Disrupt the Relational Organization of Memory in Monkeys," The Journal of Neuroscience 24(44):9811-25, Society for Neuroscience, United States (Nov. 2004).
Cao, G., et al., "In Vivo Delivery of a Bcl-xl Fusion Protein Containing the Tat Protein Transduction Domain Protects Against Ischemic Brain Injury and Neuronal Apoptosis," The Journal of Neuroscience 22(13):5423-5431, Society for Neuroscience, United States (Jul. 2002).
Carelli, V., et al., "New System for the Specific Delivery and Sustained Release of Dopamine to the Brain," Journal of Controlled Release 42(3):209-216, Elsevier, United States (Dec. 1996).
Chang, R., et al., "Blood-brain Barrier Penetrating Biologic Tnf-alpha Inhibitor for Alzheimer's Disease," Molecular Pharmaceutics 14(7):2340-2349, American Chemical Society, United States (Jul. 2017).
Chaudry, C., et al., "The Major Histocompatibility Complex-related Fc Receptor for Igg (Fcrn) Binds Albumin and Prolongs Its Lifespan," The Journal of Experimental Medicine 197(3):315-322, Rockefeller University Press, United States (Feb. 2003).
Cho, J.H., et al., "G. V. W. Primed Phosphorylation of Tau at Thr 231 by Glycogen Synthase Kinase 3β (Gsk3β) Plays a Critical Role in Regulating Tau's Ability to Bind and Stabilize Microtubules," Journal of Neurochemistry 88(2):349-358, Wiley, England (Jan. 2004).
Chung, SH., et al., "Aberrant Phosphorylation in the Pathogenesis of Alzheimer's Disease," Bmb Reports 42(8):467-74, Korean Society, Korea (Aug. 2009).
Domise, M., et al., "Amp-activated Protein Kinase Modulates Tau Phosphorylation and Tau Pathology in Vivo," Scientific Reports 6:26758, Nature Publishing Group, United kingdom (May 2016).
Dong, H., et al., "Spatial Relationship Between Synapse Loss and B-amyloid Deposition in Tg2576 Mice," The Journal of Comparative Neurology 500(2):311-321, Wiley-Liss, United States (Jan. 2007).
Drubin, D., et al., "Nerve Growth Factor Induced Neurite Outgrowth in Pc12 Cells Involves the Coordinate Induction of Microtubule Assembly and Assembly-promoting Factors," The Journal of Cell Biology 101(5):1790-1807, Rockefeller University Press, United States (Nov. 1985).
Duyckaerts, C., et al., "Prevalence, Incidence and Duration of Braak's Stages in the General Population: Can We Know?," Neurobiology of Aging 18(4):362-9, Elsevier, United States (Jul. 1997).
Edwards, W., et al., "Targeting the Ion Channel Kv1.3 With Scorpion Venom Peptides Engineered for Potency, Selectivity, and Half-life," The Journal of Biological Chemistry 289(33):22704-22714, American Society for Biochemistry and Molecular Biology, United States (Aug. 2014).
Egan, D.F., et al., "Phosphorylation of Ulk1 (Hatg1) by Amp-activated Protein Kinase Connects Energy Sensing to Mitophagy," Science 331(6016):456-461, American Association for the Advancement of Science, United States (Jan. 2011).
Gabathuler, R., et al., "Approaches to Transport Therapeutic Drugs Across the Blood-brain Barrier to Treat Brain Diseases," Neurobiology of Disease 37(1):48-57, Academic Press, United States (Jan. 2010).
Goedart, M., et al., "Tau Protein and the Neurofibrillary Pathology of Alzheimer's Disease," Annals of the New York Academy of Sciences 16(11):460-5, The Academy, United States (Jan. 1993).
Gomez-Isla, T., et al., "Profound Loss of Layer Ii Entorhinal Cortex Neurons Occurs in Very Mild Alzheimer's Disease," The Journal of Neuroscience 16(14):4491-4500, Society for Neuroscience, United States (Jul. 1996).
Gradishar, W.J., et al., "Phase Iii Trial of Nanoparticle Albumin-bound Paclitaxel Compared With Polyethylated Castor Oil-based Paclitaxel in Women With Breast Cancer," Journal of Clinical Oncology 23(21):7794-7803, American Society of Clinical Oncology, United States (Nov. 2005).
Grundke-Iqbal, I., et al., "Abnormal Phosphorylation of the Microtubule-associated Protein Tau (Tau) in Alzheimer Cytoskeletal Pathology," Proceedings of the National Academy of Sciences of the United States of America 83 (13):4913-4917, National Academy of Sciences, United States (Jul. 1986).
Guha, P., et al., "Ipmk Mediates Activation of Ulk Signaling and Transcriptional Regulation of Autophagy Linked to Liver Inflammation and Regeneration," Cell Reports 26(10):2692-2703, Cell Press, United States (Mar. 2019).
Gynther, M., et al., "Glucose Promoiety Enables Glucose Transporter Mediated Brain Uptake of Ketoprofen and Indomethacin Prodrugs in Rats," Journal of Medicinal Chemistry 52(10):3348-53, American Chemical Society, United States (May 2009).
Gynther, M., et al., "Large Neutral Amino Acid Transporter Enables Brain Drug Delivery via Prodrug," Journal of Medicinal Chemistry 5(10):932-936, American Chemical Society, United States (Feb. 2008).
Hanemaaijer, R., et al., "Involvement of Mature Tau Isoforms in the Stabilization of Neurites in Pc12 Cells," Journal of Neuroscience Research 30(1):163-171, Wiley Interscience, United States (Sep. 1991).
Bang Sookhee et al: "Human serum albumin fusion protein as therapeutics for targeting amyloid beta in Alzheimer's diseases", Neuroscience Letters, Elsevier, Amsterdam, NL, vol. 767, Oct. 18, 2021 (Oct. 18, 2021), XP086901808.

* cited by examiner

FIG. 3

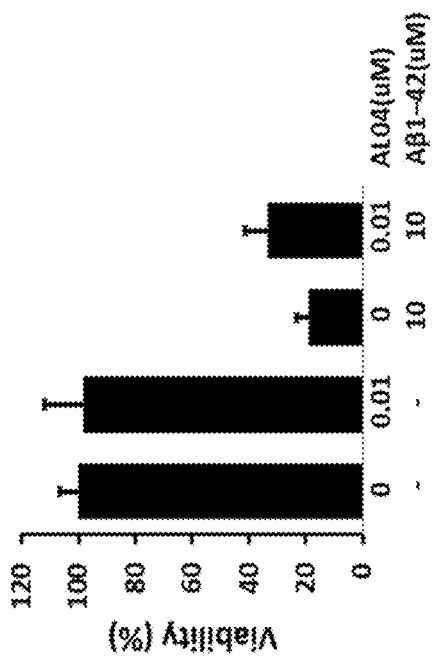
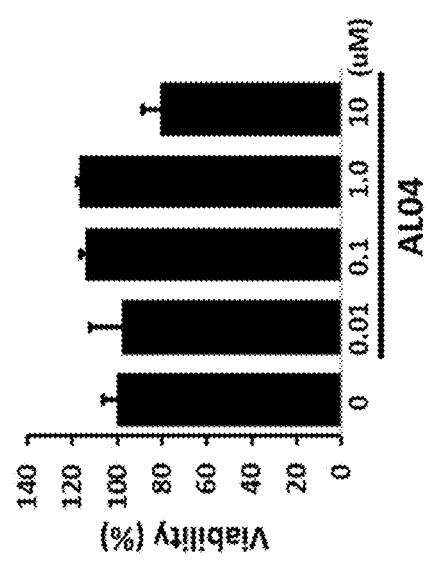
FIG. 6

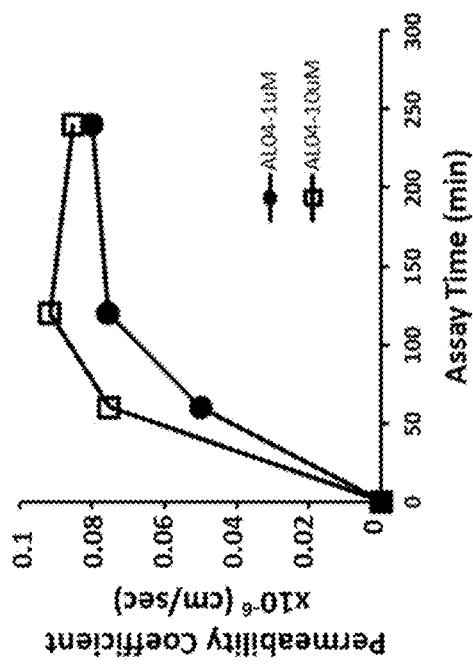
FIG. 8B
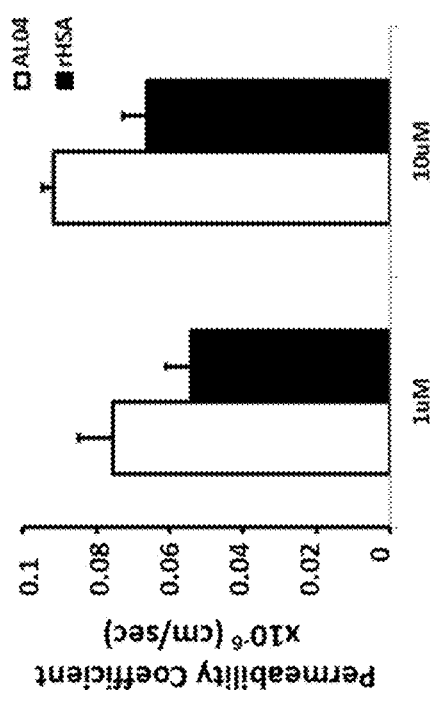
FIG. 8A
FIG. 8

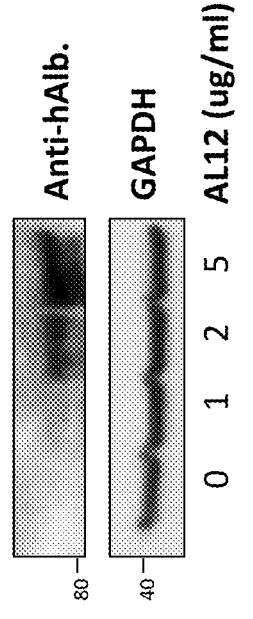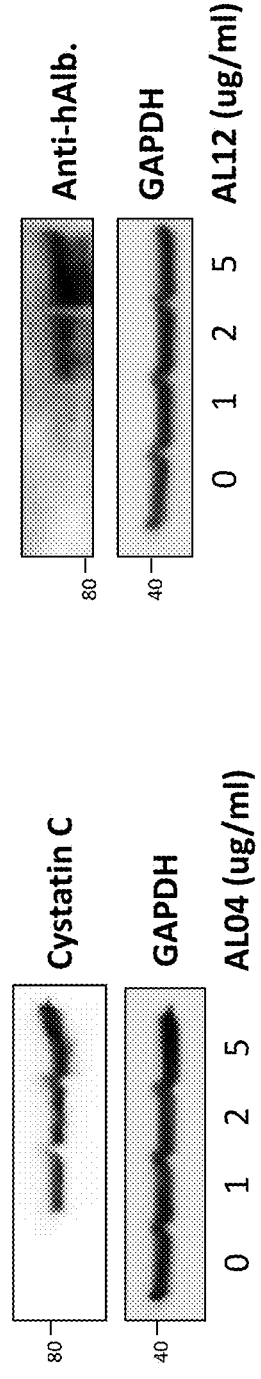
FIG. 9

| AL-04 | MOA | Carrier | CPP | construct | Expression | | Molecular Weight (kDa) |
|---|---|---|---|---|---|---|---|
| | | | | | Transient | Stable | |
| | CystatinC | Fc | dNP2 | AL-04-1 | * | ** | |
| | | | dTAT | AL-04-2 | ++ | +++ | 100 |
| | | HSA | dNP2 | AL-04-3 | +++ | +++ | |
| | | | dTAT | AL-04-4 | + | + | 80 |
| | | | | | ++++ | ++++ | |

FIG. 10

| DAT platform | | Molecular Weight (kDa) | Expression | | Purification | |
|---|---|---|---|---|---|---|
| | | | Transient expression (confirmed by Western blot) | Stable expression using MTX amplification (confirmed by Coomassie staining) | | |
| Version 1 | AL04 | 80 | ++++ | ++++ | Blue C. Chromatography → Ion exchange chromatography | Done 90% Purity |
| | AL06 | 145 | + | - | Blue C. Chromatography → Ion exchange chromatography | Not applicable |
| Version 2 | AL07 | 135 | + | ++ | Blue C. Chromatography → Ion exchange chromatography | Done 50% Purity (degradation) |
| | AL08 | 129 | + | ++ | Blue C. Chromatography → Ion exchange chromatography | Done 50% purity (degradation) |
| | AL09 | 144.5 | + | - | Blue C. Chromatography → Ion exchange chromatography | Not applicable |
| | AL10 | 156 | + | - | Blue C. Chromatography → Ion exchange chromatography | Not applicable |
| Version 2-1 | AL12 | 88 | ++++ | ++++ | Blue C. Chromatography → Ion exchange chromatography | Done 90% Purity |

FIG. 11

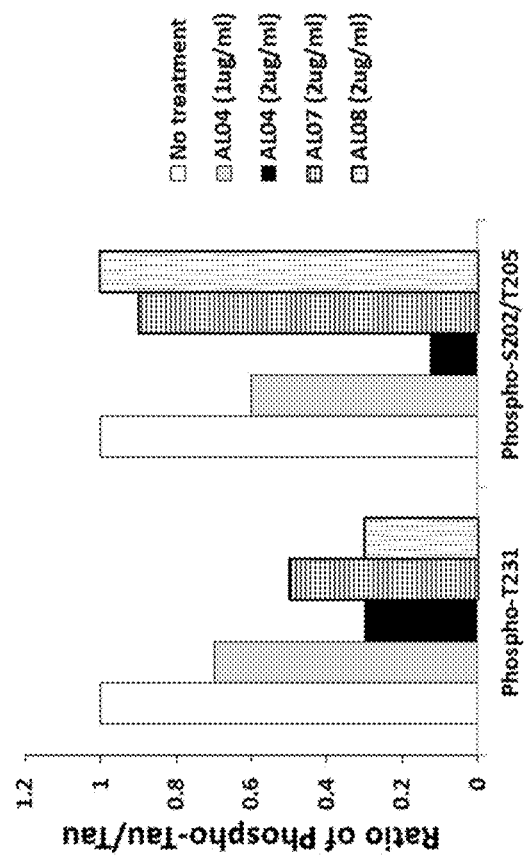
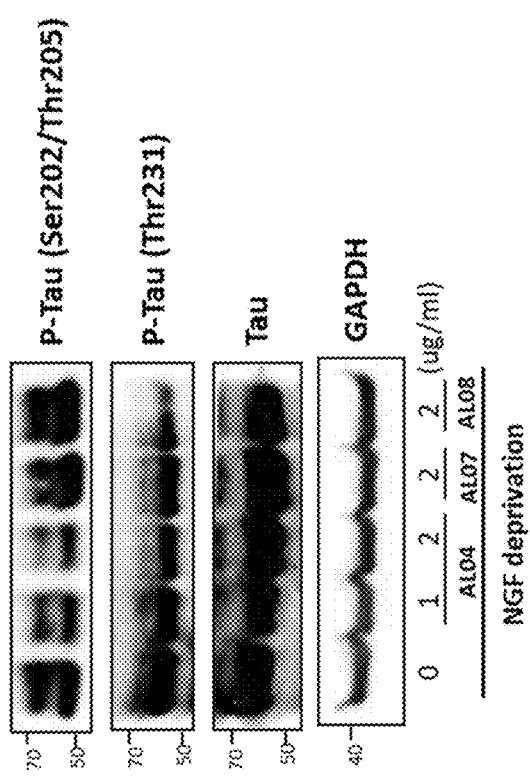
FIG. 12

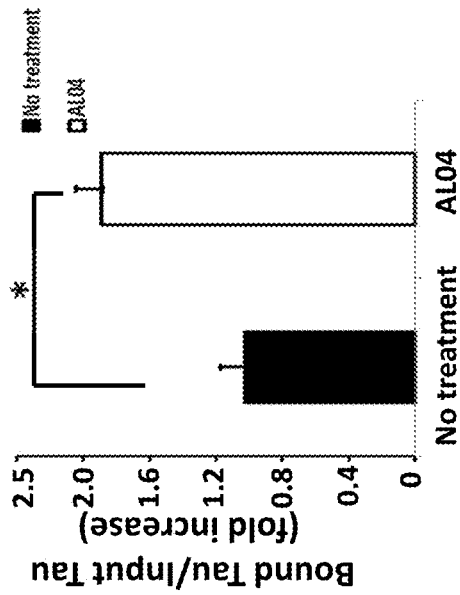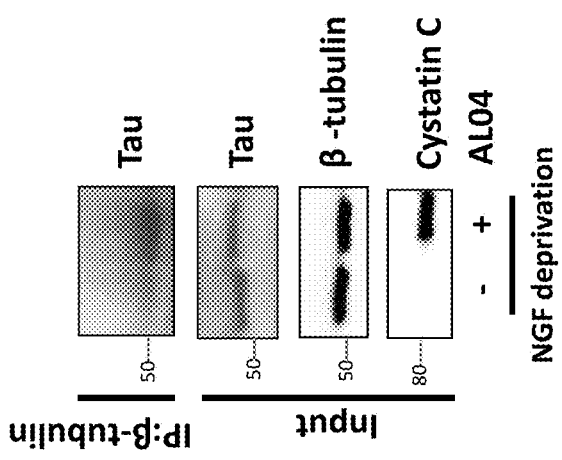
FIG. 14A
FIG. 14B
FIG. 14

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: GS linker

<400> SEQUENCE: 1

Gly Gly Ser Ala Ser
1               5

<210> SEQ ID NO 2
<211> LENGTH: 8
<212> TYPE: PRT
<213> ORGANISM: Artificial Sequence
<220> FEATURE:
<223> OTHER INFORMATION: GS linker

<400> SEQUENCE: 2

Gly Gly Gly Ser Gly Gly Gly Ser
1               5

<210> SEQ ID NO 3
<211> LENGTH: 4
<212> TYPE: PRT
<213> ORGANISM: Artificial Sequence
<220> FEATURE:
<223> OTHER INFORMATION: cleavable linker

<400> SEQUENCE: 3

Gly Phe Leu Gly
1

<210> SEQ ID NO 4
<211> LENGTH: 10
<212> TYPE: PRT
<213> ORGANISM: Artificial Sequence
<220> FEATURE:
<223> OTHER INFORMATION: cleavable linker

<400> SEQUENCE: 4

Gly Phe Leu Gly Gly Gly Gly Ser Ala Ser
1               5                   10

<210> SEQ ID NO 5
<211> LENGTH: 2211
<212> TYPE: DNA
<213> ORGANISM: Artificial Sequence
<220> FEATURE:
<223> OTHER INFORMATION: AL04

<400> SEQUENCE: 5
tccagccctg gcaagccccc tcgcctggtg ggcggcccca tggacgccag cgtggaggag      60
gagggcgtga ggcgggctct ggacttcgcc gtgggcgagt acaacaaggc ctccaatgat     120
atgtatcact ctagggctct gcaggtggtg agagcccgca agcagatcgt ggctggcgtg     180
```

| | |
|---|---|
| aactacttcc tggatgtgga gctgggcagg accacatgca ccaagacaca gccaaacctg | 240 |
| gacaattgtc cttttcacga tcagccacat ctgaagcgga aggccttctg ctctttcag | 300 |
| atctatgctg tgccctggca gggcaccatg acactgtcta agtccacctg tcaggacgct | 360 |
| ggcggctccg ctagcgatgc tcacaagtct gaggtggccc ataggttcaa ggacctgggc | 420 |
| gaggagaact ttaaggccct ggtgctgatc gctttcgccc agtacctgca gcagtgccct | 480 |
| tttgaggacc acgtgaagct ggtgaacgag gtgaccgagt tcgctaagac atgcgtggct | 540 |
| gacgagagcg ccgagaattg tgataagtct ctgcataccc tgtttggcga taagctgtgc | 600 |
| accgtggcca cactgagaga gacatatggc gagatggctg actgctgtgc caagcaggag | 660 |
| ccagagcgca acgagtgctt cctgcagcac aaggacgata cccccaatct gcctagactg | 720 |
| gtgcgcccag aggtggacgt gatgtgcacc gctttccacg ataatgagga gacatttctg | 780 |
| aagaagtacc tgtatgagat cgccaggcgg catccttact tttatgctcc agagctgctg | 840 |
| ttctttgcca agagatacaa ggccgctttc accgagtgct gtcaggccgc tgataaggcc | 900 |
| gcttgcctgc tgcccaagct ggacgagctg agagatgagg gcaaggcttc cagcgccaag | 960 |
| cagcgcctga gtgtgcttc cctgcagaag ttcggcgaga gagccttaa ggcttgggct | 1020 |
| gtggctaggc tgagccagcg gttccctaag gctgagtttg ccgaggtgtc taagctggtg | 1080 |
| accgacctga caaaggtgca caccgagtgc tgtcatggcg acctgctgga gtgcgccgac | 1140 |
| gatagggctg atctggccaa gtacatctgt gagaaccagg actctatctc ttccaagctg | 1200 |
| aaggagtgct gtgagaagcc actgctggag aagtcccatt gcatcgctga ggtggagaac | 1260 |
| gacgagatgc cagctgatct gcctccctg gccgctgact tgtgagag caggacgtg | 1320 |
| tgcaagaatt acgccgaggc taaggacgtg ttcctgggca tgtttctgta cgagtatgct | 1380 |
| agacgccacc ctgactacag cgtggtgctg ctgctgagac tggccaagac ctatgagacc | 1440 |
| acactggaga agtgctgtgc cgctgccgat ccacatgagt gctatgctaa ggtgttcgac | 1500 |
| gagtttaagc ccctggtgga ggagcctcag aacctgatca gcagaattg tgagctgttt | 1560 |
| gagcagctgg gcgagtacaa gttccagaac gccctgctgg tgcgctatac aaagaaggtg | 1620 |
| ccacaggtgt ctacccccac actggtggag gtgtccagga tctgggcaa ggtcggcagc | 1680 |
| aagtgctgta agcaccctga ggctaagcgg atgccatgcg ccgaggatta cctgtccgtg | 1740 |
| gtgctgaatc agctgtgcgt gctgcatgag aagaccccag tgagcgacag ggtgaccaag | 1800 |
| tgctgtacag agtctctggt gaacaggcgg ccctgctttt ccgctctgga ggtggatgag | 1860 |
| acatatgtgc ctaaggagtt caatgctgag accttcacat ttcacgccga catctgtacc | 1920 |
| ctgagcgaga aggagcggca gatcaagaag cagacagccc tggtggagct ggtgaagcat | 1980 |
| aagcccaagg ctaccaagga gcagctgaag gccgtgatgg acgatttcgc tgcctttgtg | 2040 |
| gagaagtgct gtaaggctga cgataaggag acatgctttg ccgaggaggg caagaagctg | 2100 |
| gtggctgcct ctcaggctgc cctgggactg gcttcctgg atacgctag gaaggctgct | 2160 |
| aggcaggccc gggcttatgc taggaaggct gctagacagg ctcgcgccgg c | 2211 |

<210> SEQ ID NO 6
<211> LENGTH: 737
<212> TYPE: PRT
<213> ORGANISM: Artificial Sequence
<220> FEATURE:
<223> OTHER INFORMATION: AL04

<400> SEQUENCE: 6

Ser Ser Pro Gly Lys Pro Pro Arg Leu Val Gly Gly Pro Met Asp Ala

```
1               5                   10                  15
Ser Val Glu Glu Glu Gly Val Arg Arg Ala Leu Asp Phe Ala Val Gly
                20                  25                  30
Glu Tyr Asn Lys Ala Ser Asn Asp Met Tyr His Ser Arg Ala Leu Gln
                35                  40                  45
Val Val Arg Ala Arg Lys Gln Ile Val Ala Gly Val Asn Tyr Phe Leu
        50                  55                  60
Asp Val Glu Leu Gly Arg Thr Thr Cys Thr Lys Thr Gln Pro Asn Leu
65                  70                  75                  80
Asp Asn Cys Pro Phe His Asp Gln Pro His Leu Lys Arg Lys Ala Phe
                    85                  90                  95
Cys Ser Phe Gln Ile Tyr Ala Val Pro Trp Gln Gly Thr Met Thr Leu
                100                 105                 110
Ser Lys Ser Thr Cys Gln Asp Ala Gly Gly Ser Ala Ser Asp Ala His
                115                 120                 125
Lys Ser Glu Val Ala His Arg Phe Lys Asp Leu Gly Glu Glu Asn Phe
130                 135                 140
Lys Ala Leu Val Leu Ile Ala Phe Ala Gln Tyr Leu Gln Gln Cys Pro
145                 150                 155                 160
Phe Glu Asp His Val Lys Leu Val Asn Glu Val Thr Glu Phe Ala Lys
                    165                 170                 175
Thr Cys Val Ala Asp Glu Ser Ala Glu Asn Cys Asp Lys Ser Leu His
                180                 185                 190
Thr Leu Phe Gly Asp Lys Leu Cys Thr Val Ala Thr Leu Arg Glu Thr
                195                 200                 205
Tyr Gly Glu Met Ala Asp Cys Cys Ala Lys Gln Glu Pro Glu Arg Asn
                210                 215                 220
Glu Cys Phe Leu Gln His Lys Asp Asp Asn Pro Asn Leu Pro Arg Leu
225                 230                 235                 240
Val Arg Pro Glu Val Asp Val Met Cys Thr Ala Phe His Asp Asn Glu
                    245                 250                 255
Glu Thr Phe Leu Lys Lys Tyr Leu Tyr Glu Ile Ala Arg Arg His Pro
                260                 265                 270
Tyr Phe Tyr Ala Pro Glu Leu Leu Phe Phe Ala Lys Arg Tyr Lys Ala
            275                 280                 285
Ala Phe Thr Glu Cys Cys Gln Ala Ala Asp Lys Ala Ala Cys Leu Leu
            290                 295                 300
Pro Lys Leu Asp Glu Leu Arg Asp Glu Gly Lys Ala Ser Ser Ala Lys
305                 310                 315                 320
Gln Arg Leu Lys Cys Ala Ser Leu Gln Lys Phe Gly Glu Arg Ala Phe
                325                 330                 335
Lys Ala Trp Ala Val Ala Arg Leu Ser Gln Arg Phe Pro Lys Ala Glu
            340                 345                 350
Phe Ala Glu Val Ser Lys Leu Val Thr Asp Leu Thr Lys Val His Thr
            355                 360                 365
Glu Cys Cys His Gly Asp Leu Leu Glu Cys Ala Asp Asp Arg Ala Asp
        370                 375                 380
Leu Ala Lys Tyr Ile Cys Glu Asn Gln Asp Ser Ile Ser Ser Lys Leu
385                 390                 395                 400
Lys Glu Cys Cys Glu Lys Pro Leu Leu Glu Lys Ser His Cys Ile Ala
                405                 410                 415
Glu Val Glu Asn Asp Glu Met Pro Ala Asp Leu Pro Ser Leu Ala Ala
                420                 425                 430
```

Asp Phe Val Glu Ser Lys Asp Val Cys Lys Asn Tyr Ala Glu Ala Lys
            435                 440                 445

Asp Val Phe Leu Gly Met Phe Leu Tyr Glu Tyr Ala Arg Arg His Pro
        450                 455                 460

Asp Tyr Ser Val Val Leu Leu Leu Arg Leu Ala Lys Thr Tyr Glu Thr
465                 470                 475                 480

Thr Leu Glu Lys Cys Cys Ala Ala Ala Asp Pro His Glu Cys Tyr Ala
                485                 490                 495

Lys Val Phe Asp Glu Phe Lys Pro Leu Val Glu Pro Gln Asn Leu
            500                 505                 510

Ile Lys Gln Asn Cys Glu Leu Phe Glu Gln Leu Gly Glu Tyr Lys Phe
            515                 520                 525

Gln Asn Ala Leu Leu Val Arg Tyr Thr Lys Lys Val Pro Gln Val Ser
530                 535                 540

Thr Pro Thr Leu Val Glu Val Ser Arg Asn Leu Gly Lys Val Gly Ser
545                 550                 555                 560

Lys Cys Cys Lys His Pro Glu Ala Lys Arg Met Pro Cys Ala Glu Asp
                565                 570                 575

Tyr Leu Ser Val Val Leu Asn Gln Leu Cys Val Leu His Glu Lys Thr
            580                 585                 590

Pro Val Ser Asp Arg Val Thr Lys Cys Cys Thr Glu Ser Leu Val Asn
            595                 600                 605

Arg Arg Pro Cys Phe Ser Ala Leu Glu Val Asp Glu Thr Tyr Val Pro
        610                 615                 620

Lys Glu Phe Asn Ala Glu Thr Phe Thr Phe His Ala Asp Ile Cys Thr
625                 630                 635                 640

Leu Ser Glu Lys Glu Arg Gln Ile Lys Lys Gln Thr Ala Leu Val Glu
                645                 650                 655

Leu Val Lys His Lys Pro Lys Ala Thr Lys Glu Gln Leu Lys Ala Val
            660                 665                 670

Met Asp Asp Phe Ala Ala Phe Val Glu Lys Cys Cys Lys Ala Asp Asp
        675                 680                 685

Lys Glu Thr Cys Phe Ala Glu Glu Gly Lys Lys Leu Val Ala Ala Ser
        690                 695                 700

Gln Ala Ala Leu Gly Leu Gly Phe Leu Gly Tyr Ala Arg Lys Ala Ala
705                 710                 715                 720

Arg Gln Ala Arg Ala Tyr Ala Arg Lys Ala Arg Gln Ala Arg Ala
                725                 730                 735
Gly

<210> SEQ ID NO 7
<211> LENGTH: 441
<212> TYPE: PRT
<213> ORGANISM: Homo sapiens

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

-continued

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
435                 440
```

METHODS OF DECREASING AMYLOID BETA (Aβ) PLAQUE DEPOSITION AND HYPERPHOSPHORYLATED TAU PLAQUE DEPOSITION IN ALZHEIMER'S DISEASE USING A CYSTATIN C FUSION PROTEIN

BACKGROUND OF THE INVENTION

1. Field of the Invention

The present invention relates generally to a dual action therapeutic system for treating a central nervous system disease, such as Alzheimer's disease.

2. General Background and State of the Art

Alzheimer's disease (AD) is one of the most common neurodegenerative diseases worldwide characterized by the progressive loss of neurons, which typically leads to severe impairments in cognitive functions including memory and learning. Pathological features of AD include the presence of extracellular amyloid plaques and the formation of neurofibrillary tangles (NFTs) in the brain, resulting in neuronal dysfunction and cell death. One of the biggest challenges in the development of therapeutics for AD is achieving sufficient blood-brain barrier (BBB) penetration (Banks, 2016). The BBB is the protective interface regulating molecular, ionic and cellular traffic between the blood and the brain (Patabendige, 2013). Other molecules, like biologics such as antibodies are large in size and unable to cross BBB efficiently. Clinically, attempts so far to enhance penetration of therapeutic proteins across the BBB in quantities sufficient to treat major brain disorders have been unsuccessful (Gabathuler, 2010). It makes it very challenging to use biologics for CNS disease like AD. In recent years, various therapeutic BBB carriers have been developed for CNS diseases (Malakoutikhah, 2011), such as chemical delivery systems (Brewster, 1997; Carelli, 1996), carrier-mediated transport (Manfredini, 2002; Gynther, 2008; Gynther, 2009), and molecular Trojan horses (Boado, 2007; Boado, 2008; Boado, 2009; Boado, 2013). Cell-penetrating peptide (CPP)-mediated drug delivery is one way to enhance brain delivery. Studies in rodents in vivo revealed that conjugation of HIV-1 trans-activating transcriptor (TAT), the most well-known CPP, with a biomolecule results in a construct that was able to facilitate the delivery of biomacromolecules across the BBB (Cao, 2002; Kilic, 2002; Banks, 2005).

However, the therapeutic efficacy of these delivery systems is not satisfactory because of their limited penetration and retention ability. The drug concentration in the diseased sections is much lower than the threshold for therapy. To address these problems, receptor-mediated BBB delivery systems have been considered as a powerful strategy to promote BBB penetration efficacy. Many researchers have focused on searching for specific receptors which are overexpressed on the BBB cell membrane to gain access to the brain with the required concentration for therapy (Wang, 2017).

Recently, new biologics in preclinical and clinical study were shown to enter the brain and shrink amyloid beta plaques (Sevigny, 2016; Reiman, 2016; Chang, 2017). As biologics become prominent approaches as therapeutics for AD, novel strategies that promote their delivery to the brain are needed. Use of endogenous transport systems is an untapped strategy in drug delivery to the brain (Banks, 2012).

Alzheimer's disease (AD) is characterized by the extracellular deposition of misfolded amyloid-β (Aβ) peptide and the intracellular formation of neurofibrillary tangles (NFTs, phosphor-Tau or p-Tau), but the strategies for lowering these pathological events remain elusive. Alzheimer's disease (AD) drug development is limited because of the presence of the blood-brain barrier (BBB), which prevents efficient uptake into the brain of most therapeutics from the blood. We developed the human serum albumin (HSA) fusion platform as therapeutic proteins, which contain BBB penetrable cell penetrating peptide (CPP, dTAT), for lowering Aβ and NFTs (p-Tau).

Microtubule-associated Tau protein is thought to participate in the formation and stabilization of microtubules (Spillantini, 2013; Lee, 2001). Tau exists as a phosphoprotein, and even in healthy adult brain Tau is at least minimally phosphorylated (Seubert, 1995) however, what distinguishes AD is the scope and consistency of phosphorylation of 19 of 441 specific amino acid sequences along the Tau protein resulting in a particular phosphorylation signature and a greater burden of phosphor-Tau in AD brain (Augustinack, 2002; Neddens, 2018; Medina, 2015). It has been reported that the magnitude of the difference in phosphor-Tau burden between AD and healthy adult brain has 3 to 4 fold increase in the number of moles of phosphate per mole of Tau (Ksiczak, 1992). The neurofibrillary tangle (NFTs), consisting of hyperphosphorylated forms of Tau that is assembled into paired helical filaments (PHFs), is the relevant pathologic feature in the postmortem Braak staging system of AD (Braak and Braak, 1995; Grundke-Iqbal, 1986; Kosik, 1986; Lee, 1991; Braak, 1995). Tangles are the only pathologic finding in AD demonstrated to correlate topographically and quantitatively with clinical symptomatology (Arriagada, 1992; Braak, 1991; Goedert, 1993; Ballatore, 2007).

Tau expression is high in non-myelinated cortical axons, especially in the regions of the brain that are involved in memory consolidation such as the limbic cortex including the hippocampus (Trojanowski, 1989). Hyperphosphorylation of Tau causes the protein to detach from the microtubules, thereby destabilizing microtubules and compromising axonal transport (Bramblett, 1993; Ishihara, 1999). The phosphorylation and dephosphorylation of Tau are controlled by the equilibrium of activity of protein kinases such as GSK3β, cdK5, Akt/PKB, PKA, ERK1/2, AMPK, and phosphatases, such as PP1, PP2A and PP5 (Ballatore, 2007; Chung, 2009; Wang, 2007).

AMP-activated protein kinase (AMPK) is the intracellular master energy sensor and metabolic regulator. AMPK is involved in cell energy homeostasis through the regulation of glycolytic flux and mitochondrial biogenesis (Hardie, 2011). Mammalian AMPK is a heterotrimeric complex assembled with catalytic α subunit (α1 and α2 isoform) and regulatory β (β1 and β2) and γ (γ1, γ2, γ3) subunits. AMPK is activated by cellular conditions of metabolic and its upstream kinases and inhibited by one of several phosphatases. Increased cytoplasmic AMP and Calcium levels are the major activators of neuronal AMPK signaling (Nakamura, 2001; Salminen, 2011; Steinberg, 2009). It has been reported that metabolic dysfunction and AMPK activity in the pathogenesis of AD as a regulator of both Tau phosphorylation and amyloidogenesis (Thornton, 2011; Vingtdeux, 2011). It also has been demonstrated that endogenous AMPK activation in mouse primary neurons induced an increase of Tau phosphorylation at multiple sites, where AMPK inhibition led to a rapid decrease of Tau phosphorylation (Domise, 2016).

PP2A is the most important phosphatase in the process of Tau phosphorylation; its inhibition under normal conditions is associated with the hyperphosphorylation of Tau. The in vivo activity of PP2A is downregulated by the endogenous inhibitory protein, inhibitor 2 (I2PP2A, also known as SET) (Li, 1996). In AD brain, lysosomal asparagine endopeptidase (AEP) cleaves I2PP2A protein (full-length ~39 kDa) into active ~20 kDa fragments (Rosenmann, 2014; Basurto-Islas, 2013). PP2A activity is inhibited by the interaction of the activated I2PP2A fragment with the catalytic subunit of PP2A (Arnaud, 2011). It also has been reported that fragment of I2PP2A is responsible for inhibition of PP2A activity and lead to increase in abnormal hyperphosphorylation of Tau (Basurto-Islas, 2013).

SUMMARY OF THE INVENTION

These and other objects of the invention will be more fully understood from the following description of the invention, the referenced drawings attached hereto and the claims appended hereto.

In one aspect, the present invention is directed to a method for treating a protein deficiency in the central nervous system of a subject in need thereof, comprising systemically administering to the subject a therapeutically effective dose of a fusion polypeptide comprising: (a) a first protein lack of which in a brain is correlated to Alzheimer's Disease; (b) a second protein that provides extended circulation-lifetime in vivo and (c) blood brain barrier crossing facilitating peptide; wherein the fusion polypeptide crosses the blood brain barrier (BBB). The amino acid sequence of the first protein may be covalently linked to the amino acid sequence of the second protein. The amino acid sequence of the second protein may be cleavably covalently linked to the blood brain barrier crossing facilitating peptide. The covalent linkage may be cleavable by a change in pH, or an introduced cleavage site may be glycyl phenylalanyl leucyl glycine (GFLG) (SEQ ID NO:3). In one aspect, the therapeutically effective dose may be at least about 1 to 10 mg/Kg of body weight.

In another aspect, the first protein may be a protein that decreases amyloid beta (Abeta) deposition in the brain and/or a protein that reduces level of hyperphosphorylated Tau in the brain. Alternatively, the first protein may possess a dual function of a protein that decreases amyloid beta (Abeta) deposition in the brain and reduces the level of hyperphosphorylated Tau in the brain.

In one aspect according to the invention discussed above, the first protein may be Cystatin C, low density lipoprotein receptor-related protein-1 cluster IV (LRP1-C4), soluble receptor for advanced glycation end products (sRAGE), RAGE-v, or Myelin basic protein (MBP). In particular, the first protein may be Cystatin C or RAGE-v. Further in particular, the first protein may be Cystatin C.

In another aspect, the second protein may be human serum albumin.

In another aspect, the blood brain barrier crossing facilitating peptide may be dTAT.

In another aspect, in the method discussed above, the first protein may be a protein that decreases amyloid beta (Abeta) deposition in the entorhinal cortex or hippocampus, and/or reduces level of hyperphosphorylated Tau in entorhinal cortex or hippocampus.

In particular, the fusion protein that comprises a protein that decreases amyloid beta (Abeta) deposition in the brain as the first protein is co-administered or administered sequentially with the fusion protein that comprises the protein that reduces level of hyperphosphorylated Tau in the brain as the first protein.

In yet another aspect, the present invention is directed to a method of treating a central nervous system degenerative disease in a subject in need thereof, comprising systemically administering to the subject a therapeutically effective dose of a fusion polypeptide comprising a first protein that decreases amyloid beta (Abeta) deposition in the entorhinal cortex or hippocampus, and a second protein that reduces level of hyperphosphorylated Tau in entorhinal cortex or hippocampus, wherein the fusion polypeptide comprises a protein that provides extended circulation-lifetime in vivo and blood brain barrier crossing facilitating peptide; wherein the fusion polypeptide crosses the blood brain barrier (BBB). In the method discussed above, the amino acid sequence of the protein that provides extended circulation-lifetime in vivo is cleavably covalently linked to the blood brain barrier crossing facilitating peptide. The covalent linkage may be cleavable by a change in pH, or an introduced cleavage site may be glycyl phenylalanyl leucyl glycine (GFLG). In one aspect according to the method discussed above, the therapeutically effective dose may be at least about 1-10 mg/Kg of human body weight. The disease may be Alzheimer's Disease. In particular, the first protein may be Cystatin C, low density lipoprotein receptor-related protein-1 cluster IV (LRP1-C4), soluble receptor for advanced glycation end products (sRAGE), RAGE-v, or Myelin basic protein (MBP). In another aspect, according to the invention discussed above the second protein may be Cystatin C, Pten-long, Pten-long with deleted PDZ domain, TFEB, or SIRT1. The protein that provides extended circulation-lifetime in vivo may be human serum albumin. The blood brain barrier crossing facilitating peptide may be dTAT. And the first protein in particular may be Cystatin C or RAGE-v.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 3 shows the schematic representation of HSA fusion protein (Version 2, AL06 to AL10). MOA protein for lowering β-amyloid plaque or Tau tangle (MOA1 or MOA2); GS linker (GGSAS (SEQ ID NO:1)) or GGGSGGGS (SEQ ID NO:2)); human serum albumin (HSA); cleavable linker (GFLG (SEQ ID NO:3) or GFLGGGGSAS (SEQ ID NO:4)); cell permeable peptide (CPP). Schematic illustration of AL06 (145 kDa), AL07 (135 kDa), AL08 (129 kDa), AL09 (144.5 kDa), AL10 (156 kDa) contains RAGE-V or RAGE-V-C1 as MOA1; Pten-long, Pten-long deleted PDZ domain, or TFEB, SIRT1 as MOA2, HSA as the carrier, and modified TAT peptide as CPP: The numbers on the boxes denote the amino acid numbers from the N-terminal of AL04.

FIGS. 6A-6B show that AL04 attenuates Aβ1-42-induced cell death on undifferentiated PC-12 cells. Non-specific cytotoxicity of AL04 on undifferentiated PC-12 cells (A), PC12 cells were exposed to 10 μM Aβ1-42 for 72 h in the presence or absence (control) of AL04 (CysC-HSA-TAT) (0.01 μM) (B). Cell viability was assessed by WST-8 (water-soluble tetrazolium salt) reduction assay.

FIG. 8 shows FIGS. 8A-8B show the evaluation of AL04 BBB permeability using human BBB model. (A) Evaluated the dose dependent permeability by using 1 and 10 μM of the AL04 and recombinant human serum albumin (rHSA) at 120 min. (B) compared the Permeability of the AL04 at three time-courses (60, 120, and 240 min).

FIGS. 9A-9B show that HSA-fusion proteins penetrate into cells in a dose dependent manner. PC12 cells were differentiated with 100 ng/ml NGF in 1% horse serum containing DMEM media. After 4 days, NGF deprived PC12 cells were treated with various concentrations (1-5 ug/ml) of AL04 (A) or AL12 (B) for 24 hrs. Cells were rinsed twice in ice cold DPBS (pH 7.5) and lysed. Cell lysates were subject to SDS-PAGE followed by Western blotting for Cystatin C (AL04) or anti-human serum albumin (AL12).

FIG. 10 shows choice of carrier protein and cell penetrating protein for the constructs. "*" indicates transient expression and integrity of fusion proteins as determined by Western blot in CHO-S cells; "**" indicates stable expression of fusion proteins as determined by SDS-PAGE from MTX (2000 nM) amplified in CHO-DG44 cells. Fc-fusion proteins formed dimers through the Fc region.

FIG. 11 shows a summary of dual action therapeutics (Versions 1, 2 and 2.1) for potential therapeutics development.

FIGS. 12A-12B show lowering levels of NGF deprived hyperphospho Tau by HSA-fusion protein treatment in PC12 cells. (A) Representative blots of phospho-Tau (Ser 202/Thr205), phospho-Tau (Thr231), and total Tau upon the treatment of NGF deprived PC12 cells with AL04, AL07, or AL08 for 24 hrs. GAPDH was used as loading control. (B) Quantitative analysis of the ratio of phosphorylation level of Tau at Ser202/Thr205 and Thr231 normalized against total Tau.

FIGS. 14A-14B show that AL04 treatment increases interaction of Tau-tubulin in NGF deprived PC12 cells. (A) PC12 cells were differentiated with 100 ng/ml NGF in 1% horse serum containing DMEM media. After 4 days, NGF deprived PC12 cells were treated with or without 1 ug/ml AL04 for 24 hr. Cells were then lysed and subjected to immunoprecipitation using anti-beta tubulin antibody. The immunoprecipitates were probed with anti-Tau antibody. Input lysate lanes were 1% of the total lysate and showed equal loading of protein. The cell lysates were subjected to Western blotting for total Tau, beta-tubulin, and Cystatin C (for AL04). Relative quantification of bound Tau to beta-tubulin are shown in (B). Values are normalized by total levels of input total Tau and expressed as means+/−SE of 3 determinations. "*", P<. 001, Student's t test.

DETAILED DESCRIPTION OF THE PREFERRED EMBODIMENTS

Figure 1:
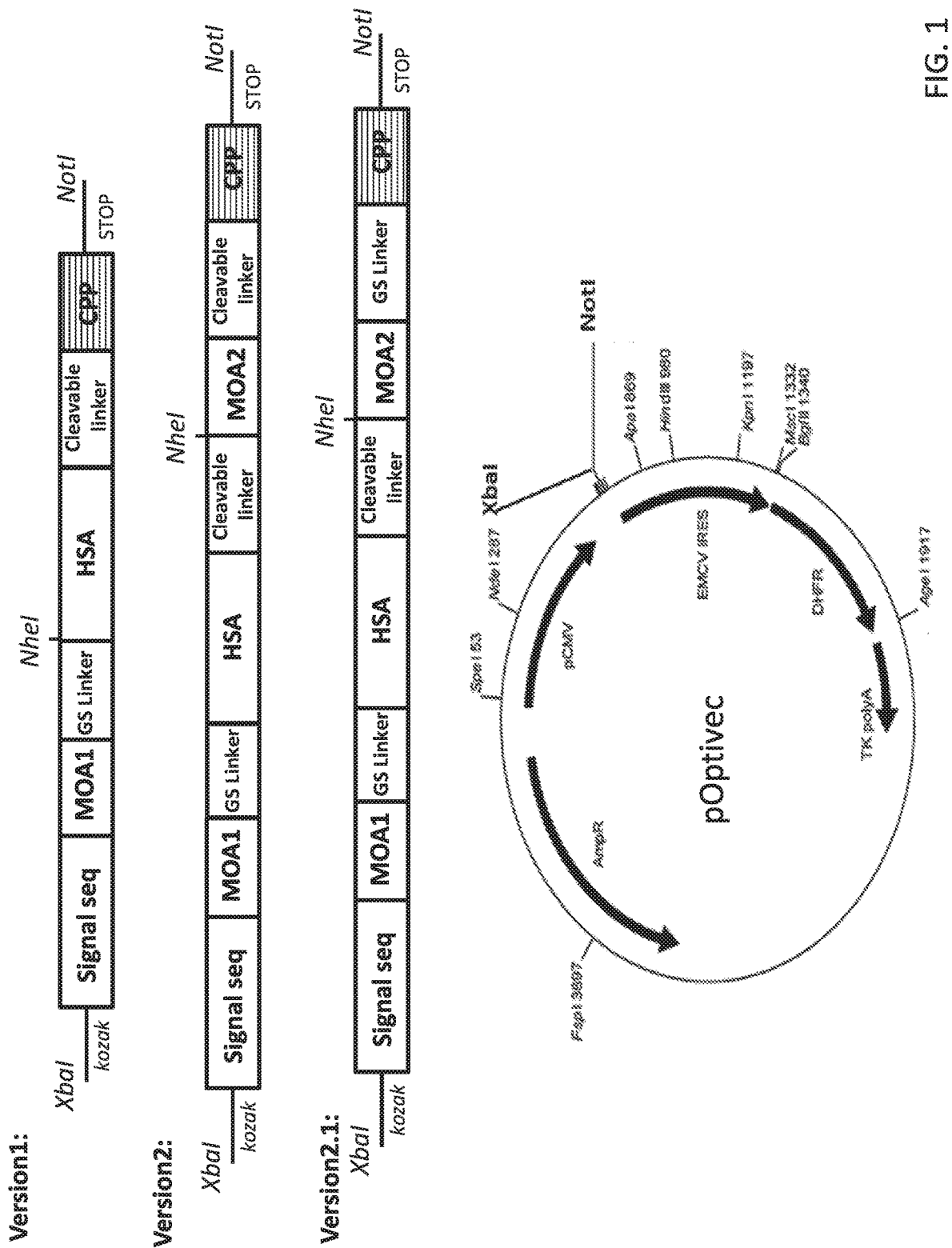
FIG. 1 shows the construct of pOptivec/HSA-fusion plasmid to express Human serum albumin fusion proteins Version 1 or 2. The bicistronic pOptivec/HSA-fusion plasmid contains the HSA fusion protein version 1 (or 2) and the selection marker DHFR. Restriction sites used for cloning procedures are in italics.
Figure 2:
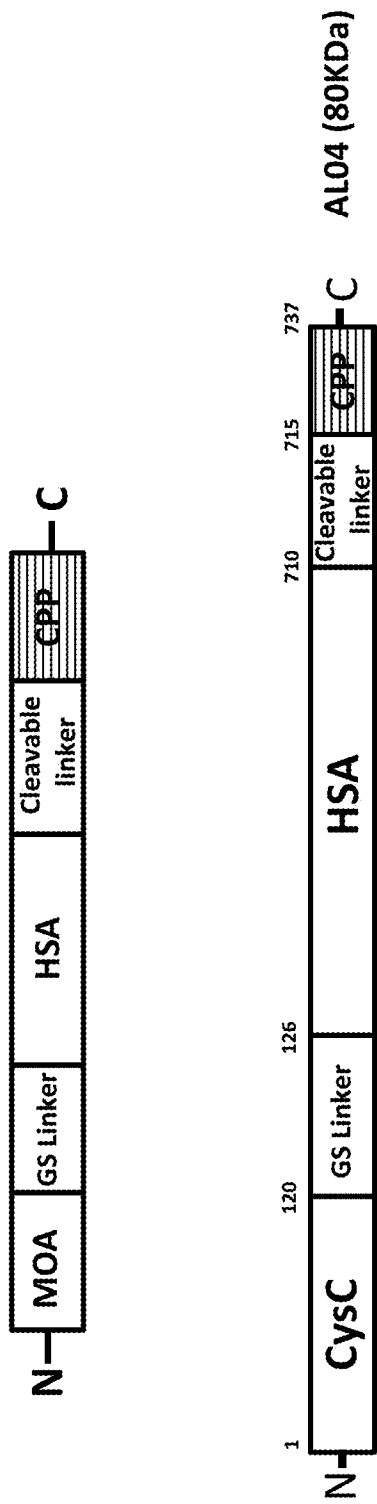
FIG. 2 shows schematic representation of HSA fusion protein (Version 1), including MOA (mechanism of action) protein for lowering β-amyloid plaque or Tau tangle; GS linker (GGSAS (SEQ ID NO:1) or GGGSGGGS (SEQ ID NO:2)); HSA (human serum albumin); cleavable linker (GFLG) (SEQ ID NO:3); horizontal line is CPP (cell permeable peptide). Schematic illustration of AL04 (80 kDa) contains Cystatin C as MOA, HSA, and modified TAT peptide as CPP. The numbers on the boxes denote the amino acid numbers from the N-terminus of the fusion protein.

The present application discloses making a fusion polypeptide that crosses the blood-brain barrier to treat a central nervous disease, in particular neurodegenerative disease such as Alzheimer's Disease, Parkinson's Disease or Huntington's Disease, most particularly Alzheimer's Disease. In some embodiments at least about 100 ug or at least about 1 mg/kg of body weight, at least bout 2 mg/kg or 3 mg/kg, 4 mg/kg or 5 mg/kg or more, of the fusion polypeptide is delivered to the human body intraperitoneally, of which it is expected that about 0.01 percent of the amount administered will be localized in the brain. In some embodiments, the therapeutically effective dose of the fusion polypeptide comprises at least about 0.5 mg/Kg of body weight. In some embodiments, systemic administration is parenteral, intravenous, subcutaneous, intramuscular, trans-nasal, intra-arterial, transdermal, or respiratory.

"Treatment" or "treating" as used herein includes achieving a therapeutic benefit and/or a prophylactic benefit. By therapeutic benefit is meant eradication or amelioration of the underlying disorder or condition being treated. For example, in an individual with Alzheimer's Disease, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of Alzheimer's Disease), or decreasing the likelihood of occurrence of a condition. As used herein, "treating" or "treatment" includes prophylaxis.

As used herein, "treatment protein" means the treatment active protein component of a fusion polypeptide.

As used herein, "fusion polypeptide" is a polypeptide construct in which multiple protein components are fused to create a polypeptide that is able to cross BBB and provide long lasting activity for the treatment protein.

As used herein, the term "effective amount" can be an amount, which when administered systemically, is sufficient to effect beneficial or desired results in the CNS, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions include, but are not limited to, neurodegeneration. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician. Such amounts are readily ascertained by one of ordinary skill in the art and will a therapeutic effect when administered in accordance with the present invention. Factors which influence what a therapeutically effective amount will be include, the Alzheimer's Disease specific activity of the fusion polypeptide administered, its absorption profile (e.g., its rate of uptake into the brain), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from Alzheimer's Disease.

In some embodiments, a pharmacological composition comprising the fusion polypeptide is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in Remington's Pharmaceutical Sciences, Gennaro, A R, ed., 20th edition, 2000: Williams and Wilkins PA, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an .alpha. carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides.

As regards "linkers" that link the various polypeptide components of the fusion polypeptide, in some embodiments, the linker comprises glycine, serine, and/or alanine residues in any combination or order. In some cases, the combined percentage of glycine, serine, and alanine residues in the linker is at least 5%, 10%, 15%, 20%, 25%, 30%, 40%, 50%, 60%, 70%, 75%, 80%, 90%, or 95% of the total number of residues in the linker. In some preferred embodiments, the combined percentage of glycine, serine, and alanine residues in the linker is at least 50%, 60%, 70%, 75%, 80%, 90%, or 95% of the total number of residues in the linker. In some embodiments, any number of combinations of amino acids (including natural or synthetic amino acids) can be used for the linker. In some embodiments, a three amino acid linker is used. In some embodiments, the linker has the sequence Ser-Ser-Ser. In some embodiments, a two amino acid linker comprises glycine, serine, and/or alanine residues in any combination or order (e.g., Gly-Gly, Ser-Gly, Gly-Ser, Ser-Ser. Ala-Ala, Ser-Ala, or Ala-Ser linker). In some embodiments, a two amino acid linker consists of one glycine, serine, and/or alanine residue along with another amino acid (e.g., Ser-X, where X is any known amino acid). In still other embodiments, the two-amino acid linker consists of any two amino acids (e.g., X-X), except gly, ser, or ala.

In some embodiments, a linker that is greater than two amino acids in length may be used. Such linker may also comprise glycine, serine, and/or alanine residues in any combination or order, as described further herein. In some embodiments, the linker consists of one glycine, serine, and/or alanine residue along with other amino acids (e.g., Ser-nX, where X is any known amino acid, and n is the number of amino acids). In still other embodiments, the linker consists of any two amino acids (e.g., X-X). In some embodiments, said any two amino acids are Gly, Ser, or Ala, in any combination or order, and within a variable number of amino acids intervening between them. In an example of an embodiment, the linker consists of at least one Gly. In an example of an embodiment, the linker consists of at least one Ser. In an example of an embodiment, the linker consists of at least one Ala. In some embodiments, the linker consists of at least 1, 2, 3, 4, 5, 6, 7, 8, 9, or 10 Gly, Ser, and/or Ala residues. In preferred embodiments, the linker comprises Gly and Ser in repeating sequences, in any combination or number, such as $(Gly_4Ser)_3$, or other variations.

A linker for use in the present invention may be designed by using any method known in the art. For example, there are multiple publicly-available programs for determining optimal amino acid linkers in the engineering of fusion proteins. Publicly-available computer programs (such as the LINKER program) that automatically generate the amino acid sequence of optimal linkers based on the user's input of the sequence of the protein and the desired length of the linker may be used for the present methods and compositions. Often, such programs may use observed trends of naturally-occurring linkers joining protein subdomains to predict optimal protein linkers for use in protein engineering. In some cases, such programs use other methods of predicting optimal linkers.

The peptide linker sequence may include a protease cleavage site.

As used herein, "activity" includes physiological activity (e.g., ability to cross the BBB and/or therapeutic activity), or the enzymatic activity of the protein of interest that is transported in the fusion polypeptide.

The compositions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed.

The appropriate quantity of a pharmaceutical composition to be administered, the number of treatments, and unit dose will vary according to the CNS uptake characteristics of a fusion polypeptide as described herein, and according to the subject to be treated, the state of the subject and the effect desired. The person responsible for administration will, in any event, determine the appropriate dose for the individual subject.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Dual Action Therapy (DAT)

The present invention is directed to a method of treating a central nervous system disease, in particular, Alzheimer's Disease by administering a construct that is described in the present application that has dual action to the patient. Such dual action therapy includes administering a construct that express (i) a molecule that decreases amyloid beta (Abeta) deposition and/or (ii) a molecule that reduces level of hyperphosphorylated Tau in the brain. Both components may be expressed from a single construct.

Alternatively, the present invention is also directed to a method of treating a central nervous system disease, in particular, Alzheimer's Disease by administering more than one construct, each construct containing either a molecule that (i) decreases amyloid beta (Abeta) deposition and/or (ii) reduces level of hyperphosphorylated Tau in the brain. Such constructs may be co-administered or administered sequentially, and as such may exhibit dual action to the patient. Such dual action therapy includes providing a molecule that (i) decreases amyloid beta (Abeta) deposition and/or (ii) reduces level of hyperphosphorylated Tau in the brain as described in the present application.

Activity of AL04

Amyloid beta accumulation has been linked often to neuronal dysfunction and neuronal loss during the pathogenesis of AD (Hensley, 1994). In this study, we first examined whether Human serum albumin fusion protein (AL04, CysC-HSA-dTAT) could protect PC12 cells from A$\beta$1-42-induced toxicity. Our results showed that 10 μM A$\beta$1-42 significantly reduced cell viability.

In a second set of experiments, we subjected PC12 cells to the presence of NGF and once they were differentiated, cells were treated for 72 h with A$\beta$1-42 in the presence or absence of AL04. As it was observed in undifferentiated cells, AL04 elicited a significant protective effect in the presence of A$\beta$1-42; however, the percentage of protection was lower than in the case of undifferentiated cells due to differentiated PC12 cells showing less sensitivity to A$\beta$1-42.

From clinical use to preclinical study, a few drugs used in AD treatment are known to take advantage of transport systems. Donepezil and probably other cholinesterase inhibitors, one of only two classes of drugs approved for the treatment of AD, is transported across the BBB by an organic cation transporter, most likely that for choline (Kang 2005; Kim, 2010). As a proof of concept of whether BBB penetration is a key factor of therapeutic biologics for Alzheimer treatment, we report here for the first time HSA-based therapeutic biologics containing tandem repeat HIV-1 trans-activating transcriptor (dTAT) peptides, and its effect in an in vitro human BBB model. We have discovered that dTAT played a role to facilitate the delivery of high molecular weight proteins across the BBB.

The advantages of our HSA fusion platform can be listed as follows: (1) HSA charges the delivery shuttle with pH-dependent FcRn recycling/transcytosis and therefore has a much longer circulation-lifetime in vivo (Sand, 2015) (2) the mechanism of dTAT entering the CNS is the temporary disruption of the BBB mainly by decreasing the expression of and altering the distribution of tight junction proteins or interaction between dTAT and heparan sulfate proteoglycan on the surface of endothelial cells (András, 2005; Xu, 2012; Zhong. 2012; Toschi, 2001) (3) the model protein core in the construct can be replaced by any type of active protein including Cystatin C (CysC), low density lipoprotein receptor-related protein-1 cluster IV (LRP1-C4), phosphatase and tensin homolog on chromosome ten (Pten), soluble receptor for advanced glycation end products (sRAGE), or Myelin basic protein (MBP), which allow the delivery system with additional therapeutic effects for AD and other CNS diseases (Sundelof, 2008; van Kasteren, 2011; Basurto-Islas, 2013; Tizon, 2010; Sagare, 2013; Zhao, 2016; Zhang, 2006; Zong. 2010; Liao, 2009).

In summary, we demonstrated for the first time that human serum albumin fusion protein harboring dTAT such as AL04 exerts an inhibitory effect on the adverse effects in Aβ1-42-treated PC12 cells. We found that dTAT of AL04 plays a role to facilitate the delivery of high molecular weight proteins across in vitro model human BBB, and that it is useful tool for proof of concept as an alternative to in vivo model. It is demonstrated that human serum albumin fusion proteins can significantly improve neuroprotection and blood-brain barrier permeability, thus providing a useful platform for drug development of AD treatment.

AL04 reading frame has the following nucleic acid (2211 bases) and amino acid sequences (737 amino acid residues).

(SEQ ID NO: 5)
tccagccctggcaagcccctcgcctggtgggcggcccatggacgc cagcgtggaggaggagggcgtgaggcgggctctggacttcgccgtgg gcgagtacaacaaggcctccaatgatatgtatcactctagggctctg caggtggtgagagcccgcaagcagatcgtggctggcgtgaactactt cctggatgtggagctgggcaggaccacatgcaccaagacacagccaa acctggacaattgtccttttcacgatcagccacatctgaagcggaag gccttctgctcttttcagatctatgctgtgccctggcagggaccat gacactgtctaagtccacctgtcaggacgctggcggctccgctagcg atgctcacaagtctgaggtggcccataggttcaaggacctgggcgag gagaactttaaggccctggtgctgatcgctttcgcccagtacctgca gcagtgccctttgaggaccacgtgaagctggtgaacagaggtgaccg agttcgctaagacatgcgtggctgacgagagcgccgagaattgtgat aagtctctgcatacccctgtttggcgataagctgtgcaccgtggccac actgagagagacatatggcgagatggctgactgctgtgccaagcagg agccagagcgcaacgagtgcttcctgcagcacaaggacgataacccc aatctgcctagactggtgcgcccagaggtggacgtgatgtgcaccgc tttccacgataatgaggagacatttctgaagaagtacctgtatgaga tcgccaggcggcatccttactttatgctccagagctgctgttcttt gccaagagatacaaggccgctttcaccgagtgctgtcaggccgctga taaggccgcttgcctgctgcccaagctggacgagctgagagatgagg gcaaggcttccagcgccaagcagcgcctgaagtgtgcttccctgcag aagttcggcgagagagcctttaaggcttgggctgtggctaggctgag ccagcggttccctaaggctgagtttgccgaggtgtctaagctggtga ccgacctgacaaaggtgcacaccgagtgctgtcatggcgacctgctg gagtgcgccgacgatagggctgatctggccaagtacatctgtgagaa ccaggactctatctcttccaagctgaaggagtgctgtgagaagccac tgctggagaagtcccattgcatcgctgaggtggagaacgacgagatg ccagctgatctgccctccctggccgctgactttgtggagagcaagga cgtgtgcaagaattacgccgaggctaaggacgtgttcctgggcatgt ttctgtacgagtatgctagacgccaccctgactacagcgtggtgctg ctgctgagactggccaagacctatgagaccacactggagaagtgctg tgccgctgccgatccacatgagtgctatgctaaggtgttcgacgagt ttaagcccctggtggaggagcctcagaacctgatcaagcagaattgt gagctgtttgagcagctgggcgagtacaagttccagaacgccctgct ggtgcgctatacaaagaaggtgccacaggtgtctaccccacactgg tggaggtgtccaggaatctgggcaaggtcggcagcaagtgctgtaag cacccctgaggctaagcggatgccatgcgccgaggattacctgtccgt ggtgctgaatcagctgtgcgtgctgcatgagaagacccagtgagcg acagggtgaccaagtgctgtacagagtctctggtgaacaggcggccc tgcttttccgctctggaggtggatgagacatatgtgcctaaggagtt caatgctgagaccttcacatttcacgccgacatctgtaccctgagcg agaaggagcggcagatcaagaagcagacagccctggtggagctggtg aagcataagcccaaggctaccaaggagcagctgaaggccgtgatgga cgatttcgctgcctttgtggagaagtgctgtaaggctgacgataagg agacatgctttgccgaggagggcaagaagctggtggctgcctctcag gctgccctgggactgggcttcctgggatacgctaggaaggctgctag gcaggcccgggcttatgctaggaaggctgctagacaggctcgcgccg gc Amino Acid Sequence of AL04 (737 Amino Acid)

(SEQ ID NO: 6)
SSPGKPPRLVGGPMDASVEEEGVRRALDFAVGEYNKASNDMYHSRAL

QVVRARKQIVAGVNYFLDVELGRTTCTKTQPNLDNCPFHDQPHLKRK

AFCSFQIYAVPWQGTMTLSKSTCQDAGGSASDAHKSEVAHRFKDLGE

ENFKALVLIAFAQYLQQCPFEDHVKLVNEVTEFAKTCVADESAENCD

KSLHTLFGDKLCTVATLRETYGEMADCCAKQEPERNECFLQHKDDNP

NLPRLVRPEVDVMCTAFHDNEETFLKKYLYEIARRHPYFYAPELLFF

AKRYKAAFTECCQAADKAACLLPKLDELRDEGKASSAKQRLKCASLQ

KFGERAFKAWAVARLSQRFPKAEFAEVSKLVTDLTKVHTECCHGDLL

ECADDRADLAKYICENQDSISSKLKECCEKPLLEKSHCIAEVENDEM

PADLPSLAADFVESKDVCKNYAEAKDVFLGMFLYEYARRHPDYSVVL

LLRLAKTYETTLEKCCAAADPHECYAKVFDEFKPLVEEPQNLIKQNC

ELFEQLGEYKFQNALLVRYTKKVPQVSTPTLVEVSRNLGKVGSKCCK

HPEAKRMPCAEDYLSVVLNQLCVLHEKTPVSDRVTKCCTESLVNRRP

CFSALEVDETYVPKEFNAETFTFHADICTLSEKERQIKKQTALVELV

KHKPKATKEQLKAVMDDFAAFVEKCCKADDKETCFAEEGKKLVAASQ

AALGLGFLGYARKAARQARAYARKAARQARAG

In this study, we investigated the therapeutic potential of AL04 that not only improves Aβ1-42-induced toxicity but also lowers phosphor-Tau levels in PC12 cells. The PC12 cell line has been used as a general in vitro model to evaluate neuronal damage and neurotoxicity in AD. Furthermore, PC12 cells are able to provide high throughput and retain a mature neuron phenotype (Tan, 1999). The biochemistry and morphology of neuron growth factor (NGF)-induced PC12 cells are similar to neurons, and PC12 cells are particularly sensitive to Aβ peptides and NGF deprivation as well. In addition, several reports have suggested that Aβ1-42 not only leads to cytotoxicity and cell death but also induces ROS overproduction and mitochondrial dysfunction in PC12 cells (Hensley, 1994). Therefore, the PC12 cells used in our experiments provide a relevant approach to determine whether AL04 affords protection against Aβ-induced cytotoxicity and NGF deprivation.

HSA is one of the most abundant circulating proteins in the blood. It has been used as a carrier protein for therapeutics due to its long-lasting half-life in the blood stream, lack of toxicity, and facility with cellular uptake (Chaudhury, 2003; Andersen, 2014). We have chosen over 10 proteins of interest (POI) including Cystatin C (CysC), low density lipoprotein receptor-related protein-1 cluster IV (LRP1-C4), phosphatase and tensin homolog on chromosome ten (Pten), soluble receptor for advanced glycation end products (sRAGE), Myelin basic protein (MBP) and so forth, which could play an important role in either Aβ elimination or p-Tau reduction via inhibition of fibril formation and facilitate clearance. To develop HSA-fusion protein production cell line, we constructed expression vector pOptivec (Invitrogen) that contains HSA-fusion proteins (AL04, CysC-HSA-dTAT) and selection marker dihydrofolate reductase (DHFR). Stably transfected DHFR-deficient cells (DG44 cells) and methotrexate (MTX, DHFR inhibitor)-amplified cell pools were generated. We tested for proof-of concept using a purified AL04 protein. AL04 attenuated Aβ-induced cell death, reduced NGF deprivation-induced hyper-phosphorylation of Tau, and improved endogenous Tau-tubulin interaction in Pheochromocytoma (PC12) cells. We evaluated the permeability of high molecular weight protein AL04 (80 KDa) through the blood-brain barrier using a cell-based in vitro human BBB model. This BBB-crossing human serum albumin fusion protein platform is useful for drug development of AD treatment.

Therapeutic efficacy of HSA-fusion protein depends on successful delivery of a fusion protein into the cell. We examined whether Human serum albumin fusion proteins (AL04, CysC-HSA-CPP; AL12, RAGE (V)-HSA-SIRT1 (Exon4)-CPP) could penetrate into differentiated PC12 cells. We observed that different version of HSA fusion proteins (AL04 or AL12) easily penetrated into PC12 cells and also could effectively deliver their biological activity intracellularly.

In this study, we have used the differentiated PC12 cells to investigate the role of Human serum albumin fusion therapeutics (AL04) in NGF deprivation-induced hyper-phosphorylation of Tau under NGF deprivation. In undifferentiated PC12 cells, Tau is expressed at low levels, whereas stimulation with NGF leads to increases in Tau expression starting after 3 days of treatment (Drubin, 1985; Hanemaaijer, 1991). Tau is known to be required for microtubule stabilization at later stages of NGF-induced neurite elongation (Brandt, 1995; Hanemaaijer, 1991). It has been reported that there is increased levels of Tau phosphorylated (p-Tau) at Thr205 and Thr231 in Alzheimer's brain and mouse models (Wang, 2013). We investigated whether AL04 treatment reduces NGF deprivation-induced hyperphosphorylation of Tau in PC12 cells. We observed that there is highly increased levels for p-Tau Ser202/Thr205 and p-Tau Thr231 in NGF-deprived PC12 cells (data not shown). In the presence of AL04, we observed a dramatic reduction in level of phosphor-Tau at Ser202, Thr 205, and Thr231. It has been reported that PP2A activity is inhibited by the interaction of the activated I2PP2A fragment with the catalytic subunit of PP2A (Arnaud, 2011). Since AL04 treatment decreased levels of ~20 kDa fragments of I2PP2A and also p-Tau Ser202/Thr205 and p-Tau Thr231, these results suggested that AL04 (harboring Cystatin C) affects regulation of PP2A activity involved with dephosphorylation of Tau through downregulation of I2PP2A.

The mutation sites relative to the Tau protein described in the present application is of SEQ ID NO:7 below.
Human Tau: Microtubule-Associated Protein Tau Isoform 2 (NCBI Reference Sequence: NP_005901.2), 441 Amino Acid (SEQ ID NO: 7)
MAEPRQEFEVMEDHAGTYGLGDRKDQGGYTMHQDQEGDTDAGLKESP

LQTPTEDGSEEPGSETSDAKSTPTAEDVTAPLVDEGAPGKQAAAQPH

TEIPEGTTAEEAGIGDTPSLEDEAAGHVTQARMVSKSKDGTGSDDKK

AKGADGKTKIATPRGAAPPGQKGQANATRIPAKTPPAPKTPPSSGEP

PKSGDRSGYSSPGSPGTPGSRSRTPSLPTPPTREPKKVAVVRTPPKS

PSSAKSRLQTAPVPMPDLKNVKSKIGSTENLKHQPGGGKVQIINKKL

DLSNVQSKCGSKDNIKHVPGGGSVQIVYKPVDLSKVTSKCGSLGNIH

HKPGGGQVEVKSEKLDFKDRVQSKIGSLDNITHVPGGGNKKIETHKL

TFRENAKAKTDHGAEIVYKSPVVSGDTSPRHLSNVSSTGSIDMVDSP

QLATLADEVSASLAKQGL

Several studies provided evidence that phosphorylation of key sites on Tau has a strong impact on the normal function of Tau and likely contributes to its pathological role (Ksiezak-Reding, 1992; Augustinack, 2002). Phosphorylation of Tau at Thr-231 has also been shown to reduce its affinity for microtubules (Cho, 2004; Sengupta, 1998; Lin, 2007). We also observed that treatment with AL04 stabilizes microtubule-Tau interaction through reducing phospho-Tau level. Although our study does not identify the signal pathway responsible for the reduction in Tau phosphorylation associated with AL04 treatment, seemingly mediated by inhibition of AMPK activity, treatment with AL04 inhibits Tau aggregation and tangle formation in vivo. In the current report, we observed a reduction in phosphor-ULK1 (Unc51-like kinase1 at Ser555) from AL04 treatment, which suggests that AL04 may regulate autophagy through AMPK signal pathway. It has been reported that AMPK mediates autophagy activation directly by phosphorylation of the protein kinase that initiates autophagy, phosphorylates its direct substrates including ULK1 at S555 (Egan, 2011; Kim, 2011).

In conclusion, our findings demonstrate that AL04 has a significant protective effect on lowering phosphor-Tau under NGF deprivation. According to these in vitro studies, the protective effect of AL04 may be mediated by modulating Tau kinase activity (AMPK), PP2A activity and stabilizing Tau-tubulin interaction. Since Tau kinase and PP2A play an important role in NFT formation in AD, these data suggest that AL04 could alter Tau phosphorylation and thus potentially affect the accumulation of NFT in the AD brain.

Described herein are methods for delivering an effective dose of the treatment polypeptide to the CNS across the BBB by systemically administering a therapeutically effective amount of a fusion polypeptide, as described herein. Suitable systemic doses for delivery of a fusion polypeptide is based on its CNS uptake characteristics and its specific activity as described herein. Systemic administration of a fusion polypeptide to a subject suffering from a deficiency of the treatment protein is an effective approach to the non-invasive delivery of the treatment protein to the CNS.

The amount of a fusion polypeptide that is a therapeutically effective systemic dose of a fusion polypeptide depends, in part, on the CNS uptake characteristics of the fusion polypeptide to be administered, as described herein, e.g., the percentage of the systemically administered dose to be taken up in the CNS.

In some embodiments, 1% (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered fusion polypeptide is delivered to the brain as a result of its uptake from peripheral blood across the BBB. In some embodiments, at least 0.5%, (i.e., about 0.3%, 0.4%, 0.48%, 0.6%, 0.74%, 0.8%, 0.9%, 1.05, 1.1, 1.2, 1.3%, 1.5%, 2%, 2.5%, 3%, or any % from about 0.3% to about 3%) of the systemically administered dose of the fusion polypeptide is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

Accordingly, in some embodiments the invention provides methods of administering a therapeutically effective amount of a fusion polypeptide systemically, such that the amount of the fusion polypeptide to cross the BBB provides at least 3 ng of the treatment protein/mg protein in the subject's brain, e.g., 3, 5, 6, 7, 8, 9, 10, 12, 14, 16, 18, 20, 30, 40, 50 or any other value from 3 to 50 ng of treatment protein/mg protein in the subject's brain.

In one aspect, if we assume that the BBB penetration rate of is 0.01%, when 100 ug of AL04 is given to mouse, 10 ng of AL04 may be delivered to 40 mg protein of mouse brain, where mouse brain weight is 400 mg and its total protein amount is 40 mg. This may be extrapolated to humans.

In some embodiments, a therapeutically effective systemic dose comprises at least 50, 100, 200, 300, 400, 500, 600, 700, 800, 900, 1000, 1500, 2000, 2500 units per brain, or any other systemic dose from about 50 to 2500 units of the treatment protein activity per brain.

In other embodiments, a therapeutically effective systemic dose is at least about 10 units of treatment protein activity/kg body weight, at least about 10, 12, 15, 18, 25, 30, 50, 75, 100, 150, 200, 250, or any other number of units.

One of ordinary skill in the art will appreciate that the mass amount of a therapeutically effective systemic dose of a fusion polypeptide will depend, in part, on its specific activity. In some embodiments, the specific activity of a fusion polypeptide is at least 10 U/mg of protein, at least about 10, 12, 14, 16, 18, 20, 25, 30, 35, 40, 45, 50, or any other specific activity value from about 10 units/mg to about 50 units/mg.

Thus, with due consideration of the specific activity of a fusion polypeptide and the body weight of a subject to be treated, a systemic dose of the fusion polypeptide can be at least 5 mg. e.g., 5, 10, 15, 20, 25, 30, 35, 40, 45, 50, 55, 60, 65, 70, 75, 100, 125, or any other value from about 5 mg to about 125 mg of fusion polypeptide.

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration. Any suitable fusion polypeptide, as described herein, may be used.

The fusion polypeptide may be administered as part of a combination therapy. The combination therapy involves the administration of a composition of the invention in combination with another therapy for treatment or relief of symptoms typically found in a patient suffering from an Alzheimer's Disease. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

In some embodiments, the composition, e.g., a fusion polypeptide is co-administered to the patient with another medication, either within the same formulation or as a separate composition.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1. Construction of pOptivector to Express Human Serum Albumin (HSA) Fusion Protein The plasmids pOptiVec (Invitrogen, USA) were used as expression vectors. The codon-optimized synthetic gene cDNA sequences of human serum albumin (NM_000477), protein of interests: Cystatin C. NM_000099.3; Pten-long, NM_001304718; Receptor for Advanced Glycation End-products (RAGE), NM_001136.4; *Homo sapiens* transcription factor EB (TFEB), NM_007162.2; SIR1_HUMAN NAD-dependent protein deacetylase sirtuin-1 (SIRT1), NM_012238.5 as MOA1 or MOA2, and dTAT (tandem repeat TAT, TAT_HV1H2 from UniProt-P04608) as CPP were ordered from Genescript. The plasmids were treated with the restriction enzymes XbaI, NheI and NotI (Thermo, USA). Separation of the DNA fragments was performed by electrophoresis in a 0.8% agarose gel. For elution of DNA fragments from the gel, we used the Thermo gel extraction kit (Thermo, USA). Then, the generated fragments were ligated together with T4 DNA ligase (NEB, USA) to create the following expression vectors: pOptiVec-AL000.

For transfection of the highly pure isolated plasmid DNA, we used the Plasmid Midi kit (Thermo, USA). Proper assembly of the expression vector was verified by restriction analysis. The nucleotide sequences of both the genes and the adjoining regions were verified by sequencing (Genewiz, USA).

Example 2. Culturing CHO-DG44 Cell Lines

Cell cultures were carried out in 125 mL Erlenmeyer flasks in a $CO_2$ incubator operating at a speed of 125 rpm in an atmosphere of 8% $CO_2$, at a temperature of 37° C. and 95% humidity. Reseeding was performed every 3-4 days to a density of 0.3-0.5×10$^6$ cells/mL. We used CD DG44 (Life technologies, USA) serum-free media supplemented with 8 mM L-glutamine. Cell counts and viability analysis were performed after staining with trypan blue using an automatic cell counter Cellometer AutoT4 (Nexcelom Bioscience, USA).

Example 3. Stable Cell Line Development

Prior to transfection, the expression vector plasmids were linearized by FspI restriction (Thermo, USA). The dihydrofolate reductase (DHFR)-null CHO DG44 cell line was transfected with linearized pOptiVec-AL000, according to the FreeStyle MAX reagent protocol (Invitrogen, USA). At 72 hours post-transfection, transfected cells were selected for growth in the absence of hypoxanthine and thymidine (HT) CD OptiCHO™ medium (Life technologies, USA) containing 8 mM L-Glutamine (complete selection medium). Selection medium was replaced every 3~4 days with a density of 0.5×10$^6$ cells/mL until selected cell's viability was greater than 90% and then followed by two to three rounds of genomic amplification in complete medium containing stepwise increased concentration of methotrexate (MTX) at 250 nM up to 2 µM. HSA fusion protein production was determined at the end of cultivation in the selection/amplification medium using the human albumin quantitation ELISA kit (Bethyl Laboratory, USA) and SDS-PAGE.

Example 4. Shake Flask Cultures of AL04

The 2000 nM MTX amplified cells were cultivated in 500 ml disposable Erlenmeyer flask till their viabilities were greater than 90% containing 150 ml CD OptiCHO™ medium (Life technologies, USA) containing 8 mM L-Glutamine at viable cell density of 0.5×10$^6$ cells/ml. Cell densities and viabilities were determined every other day by the Trypan Blue Exclusion method using an automated cell counter, Cellometer AutoT4 (Nexcelom Bioscience, USA). For protein purification, the culture was harvested on day 10 or when cell viability dropped below 90%.

Example 5. Purification of AL04

Culture media containing Human serum albumin fusion proteins secreted from CHO-DG44 cells were filtered (0.2 µm filter) and subsequently purified by blue dye affinity chromatography followed by ion-exchange column chromatography. Briefly, filtered fusion protein containing media was applied to Blue HP column (GE) was equilibrated with 0.05M Tris buffer (pH 8.0). The column was washed with equilibration buffer to remove unbound proteins, bound fusion proteins were eluted with 10× column volumes of elution buffer (0.05M Tris, pH 8.0+1.0M NaCl). Eluted fractions were desalted using centrifugal desalting columns with 40 kDa molecular weight cut-off (Pierce). For further purification, performed ion exchange column chromatography HiTrap QFF (GE) was performed. According to manufacturer's instruction, fractions containing fusion protein were pooled and dialyzed in PBS. Purified proteins were analyzed by SDS-PAGE with purity greater than 90%. Human serum albumin fusion proteins were then filtered (0.2 µm) for sterilization and stored at −80° C. Protein concentration was determined using the Bradford method (Thermo).

Example 6. Human Albumin Quantitation ELISA 96-well ELISA plates (Bethyl laboratory, USA) were coated overnight at 4° C. with purified goat anti-human albumin coating antibody (Bethyl laboratory, USA) diluted 1:100 in a sodium bicarbonate coating buffer (pH 9.0). Blocking was achieved with 1% bovine serum albumin prepared in TBS buffer for 1 hr. After incubation, plates were washed five times with Tris buffered saline tween-20 (TBST), samples and controls were diluted in sample buffer (TBS buffer containing 1% BSA), and 100 µL of each sample was applied directly to the coated wells. A standard curve was generated with 6.5, 12.5, 25, 50, 100, 200, and 400 ng/mL using human reference serum (supplied by Bethyl) diluted in sample buffer. Microplates were incubated with 100 µL of diluted samples and standards at RT for 1 h. Then plates were washed five times with TBST buffer and incubated with 100 µL of goat anti-human albumin detection antibody conjugated with horseradish peroxidase (Bethyl) diluted 1:100,000 in sample buffer. The microplate was incubated for 1 h. After plates were washed five times, 100 ul of 3,3',5,5'-tetramethylbenzidine (TMB) substrate (Bethyl) was added, the plates were developed in the dark at RT for 15 min, and reaction was stopped with ELISA stop solution (Bethyl). Finally, the absorbance was measured at 450 nm with a Plate reader (BioTEK). Each assay was performed in triplicate, and AL04 (CysC-HSA-dTAT) protein concentrations were interpolated from the linear portion of the standard curve.

Example 7. Preparation of LC-MS/MS Analysis

8 µg of purified AL04 (CysC-HSA-dTAT) protein were loaded onto a 4%-12% gradient gel (Life Technologies). After staining the gel in Coomassie Brilliant Blue G-250 (Thermo) and rinsing in water, the AL04 (CysC-HSA-dTAT) protein band was excised from the gel for LC-MS/MS based protein identification/analysis (BioSyn). For N-terminal sequencing sample preparation, after the electrophoresis completion, protein blotting was performed by transferring to a 0.22 µm PVDF membrane (Bio-Rad) at 100 V for 90 min in NuPAGE transfer buffer containing 10% methanol. Blotted PVDF membrane were washed three times with $DDH_2O$ and stained in Ponceau S (Bio-Rad) followed by destaining in $DDH_2O$. Stained AL04 (CysC-HSA-dTAT) protein band was excised from the membrane for N-terminal sequencing (BioSyn, USA).

Example 8. PC-12 Cell Toxicity Assay as Regards Aβ1-42

Aβ1-42 (AnaSpec, USA) was dissolved in DPBS containing 0.1% $NH_4OH$ at 1 mM stock solution. Aliquots were stored at −80° C. and pre-incubated (aged) at 37° C. for 3 days for peptide aggregation.

The rat pheochromocytoma cell line (PC12) is a classic in vitro neuroendocrine cell model. Unlike primary neurons, undifferentiated PC12 cells do not require Nerve growth factor (NGF) for survival, but they respond to it by producing lengthy neurite extensions and by undergoing other neural-specific changes such as an increase of cholinergic receptor expression (Jumblatt, 1982; Amy, 1983). NGF-treated PC12 cells exhibit many of the hallmarks of differentiated neurons. PC12 cells were cultured in DMEM Medium (Gibco) supplemented with 10% (v/v) of heat-inactivated fetal bovine serum (FBS), 5% (v/v) of heat-inactivated horse serum (HS) and 1% (v/v) of penicillin and streptomycin, followed by culturing at 37° C. in a humidified atmosphere with 5% $CO_2$. The cells were taken to be used in various experiments or were passaged once they reached 80% confluence. Prior to experiments, PC12 cells were seeded at 15000 cells per well in 100 ul of 96-well plates pre-coated with poly-D-Lysine to allow the cells to adhere to the wells of the plate. For experiments in undifferentiated cells, 96-well plates were used and the drug treatments were directly started 24 h after seeding the cells. NGF-primed (neuronally differentiated) PC12 cells were grown for at least 6 days in DMEM medium plus 1% horse serum and 100 ng/ml NGF (Sigma, USA). Aβ1-42-mediated toxic effect was determined using the WST-8 reduction assay (Dojindo Molecular Technologies, USA). Briefly, cells were treated in the presence or absence of AL04 at different concentrations (0, 0.01, 0.1, 1, and 10 μM) and/or Aβ1-42 (10 μM) for additional 3 days at 37° C. After the incubation period, 10 μl of stock WST-8 was added and the incubation was continued for another 3~4 h. The A 450 of WST-8-formazan produced by the dehydrogenase activity in the living cells was measured (reference: 630 nm) using a microplate reader (BioTEK, USA).

Example 9. BBB Permeability Assay of AL04

The in vitro human BBB model (Neuromics, USA) was established using co-cultures of primary Human brain endothelial cells (HBEC), Human brain pericytes (HBPC), and Human brain astrocytes (HBAC). In vitro human BBB model kit has two sides (luminal, blood/abluminal, brain) with 12 transwell inserts (polyester membrane, 0.4 μm pore, diameter 12 mm, insert growth area: 1.12 cm$^2$). HBPC were grown on the bottom side of the inserts, HBEC were monolayered on the upper side of the inserts, and HBAC were grown on the bottom of the 12-well culture plate (Neuromics, USA). In vitro BBB model was activated according to the manufacturer's instructions for 4 days. Briefly, the medium from both luminal and abluminal (lower, brain) sides of the transwell insert was changed every other day. Before the transport experiment, the abluminal side was filled with the permeability assay medium. For the permeability assay, purified AL04 or recombinant HSA (Sigma, USA) were added to the luminal side (0.3 ml) of the transwell insert to yield a final concentration of 1 or 10 μM. Incubations were performed on orbital shaker (100 rpm) at 37° C. Samples (150 μl) were collected from the abluminal side (1.2 ml) at 60, 120 and 240 min and immediately replaced with fresh permeability assay medium. The concentrations of transported AL04 or rHSA were measured by Human albumin quantitation ELISA kit (Bethyl laboratory, USA) and analyzed using the standard curve method. Permeability coefficients ($P_e$, cm s$^{-1}$) were calculated using the equation: $P_e=(V_A/(A \times c_0)) \times (dQ/dt)$, where $V_A$ is volume of assay buffer in blood side (inside of the insert), A is the surface area of the insert (1.12 cm$^2$), $c_0$ the initial concentration of protein sample added into blood side, dQ/dt the concentration of transported protein sample in brain side in a defined time period. The permeability coefficients ($P_e$, cm s$^{-1}$) for the purified AL04 or recombinant HSA were calculated as previously described (Prades, 2015; Nakagawa, 2009).

Example 10. Results

Example 10.1. Gene Construct and Vector Design for Recombinant HSA Fusion Protein (AL04)

At the initial stage, genes encoding human serum albumin, protein of interest (e. g., Cystatin C. Pten-long as MOA1 or MOA2), and dTAT with optimized codon composition were synthesized. Gene sequences were obtained from publicly available sources (NCBI, national center for biotechnology information and UniProt, universal protein resource). pOptiVec plasmid vectors were used as carriers of the individual genes of the human serum albumin, protein of interests (e. g., Cystatin C. Pten-long as MOA1 or MOA2), and dTAT (FIGS. 1-4).

Example 10.2. Production of HSA Fusion Protein (AL04)

After suspension, CHO-DG44 cells were transfected with the linearized expression vectors, Optivec-CysC-HSA-dTAT and were detected in culture supernatants using a human albumin quantitation ELISA kit (Bethyl). The transfected CHO cells then underwent selection and MTX amplification in CD Opti CHO media containing 8 mM L-Glutamine. To achieve a high-titer production of recombinant proteins, the mammalian cell expression system popularly used in the biopharmaceutical industry, the methotrexate (MTX) amplification system (Ng, 2012) was used. During the MTX amplification process, the expression of AL04 (Optivec-CysC-HSA-dTAT) increased in the culture supernatant as human albumin is quantitated by ELISA. Cell pools at 2000 nM MTX concentration were then adapted to AL04 expression culture.

Example 10.3. Characterization of Purified AL04 Protein

Figure 5:
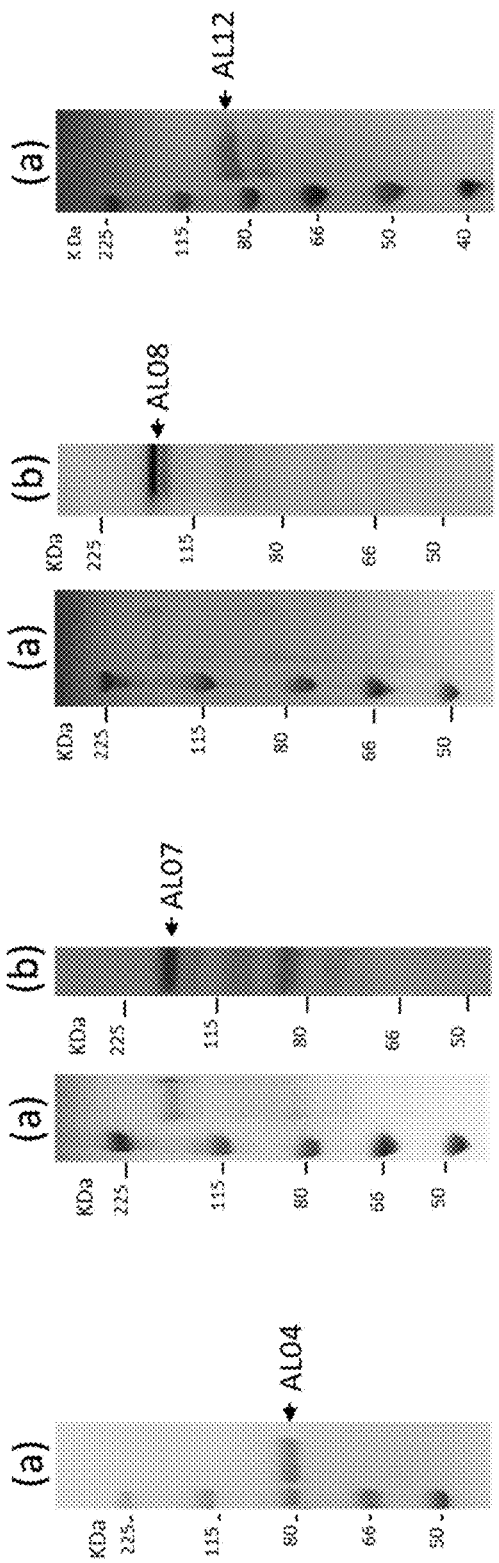
FIG. 5 shows characterization of purified AL04 (80 kDa), AL07 (135 kDa), AL08 (129 kDa), and AL12 (88 kDa) by SDS-PAGE (a) and Western blot (b). Purified samples were run on 4-12% gradient gel under reducing conditions. (a) The gel was stained with Coomassie blue. (b) The gradient gel containing each protein was transferred to the PVDF membrane for Western blotting using purified anti-human serum albumin antibody.

The identity of AL04 protein was validated by SDS-PAGE analysis (FIG. 5). The size (integrity) of the purified AL04 protein band was shown to be around 80 kDa under reducing conditions in eluent from blue column chromatography. To confirm the authenticity of AL04 protein purified from blue column, proteins were subjected to LC-MS/MS analysis (Biosyn). At least 69 unique peptides corresponding to AL04 were detected with protein coverage of 92%. To confirm the N-terminus of the AL04 protein, the unique peptide SSPGKPPRLV was observed in sample (data not shown). The analysis also confirmed that the signal peptide was correctly cleaved from the mature secreted protein. Based on the LC-MS/MS analysis and N-terminal sequencing, we confirmed that the AL04 protein purified from blue column chromatography was identical to the expressed sequence.

Example 10.4. Protective Effect of AL04 (CysC-HSA-dTAT) Against Aβ1-42-Induced Cytotoxicity We studied possible non-specific cytotoxicity of AL04 in PC12 cell culture. No modifications in cell viability were observed when AL04 was incubated alone at 0.01 μM. 0.1 μM, and 1 μM, nevertheless, concentrations as high as 10

µM AL04 reduced cell viability (FIG. 6A). In vitro studies have shown that Cystatin C binds to central domain of Aβ, which is important for Aβ structure, inhibits formation of Aβ aggregation and protects Aβ-induced toxicity (Juszczyk, 2009; Tizon, 2010). We tested whether Cystatin C containing AL04 inhibits Aβ-induced toxicity. Treatment of PC12 cells with 10 µM Aβ1-42 alone led to a significant decrease in cell viability to 20% at soluble 10 µM Aβ1-42 as compared to control cells (no Aβ1-42). However, in the presence of AL04, the Aβ1-42-induced cell death was rescued (FIG. 6B).

Figure 7:
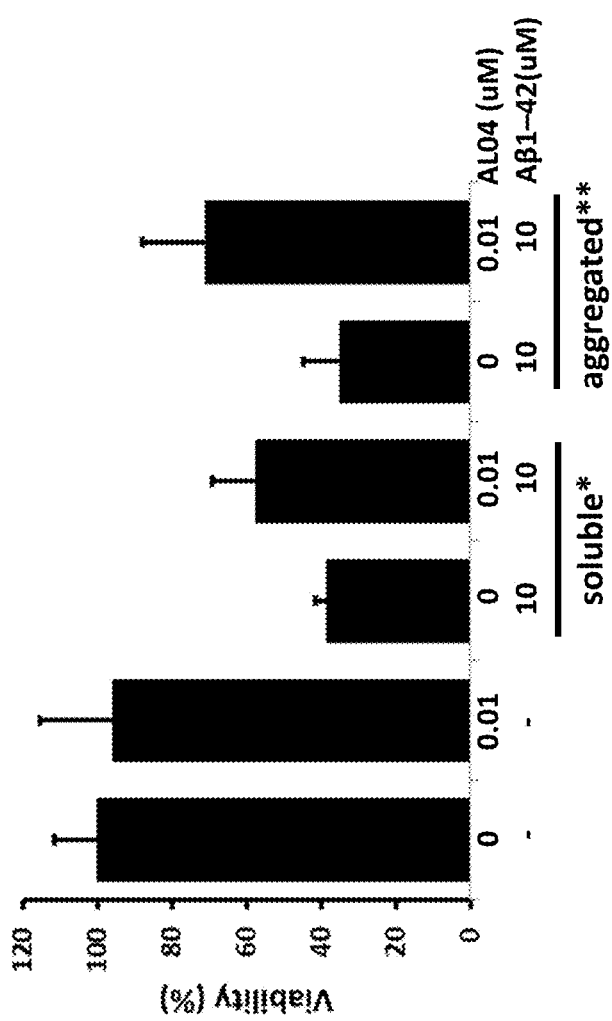
FIG. 7 shows that AL04 attenuates Aβ1-42-induced cell death on differentiated PC12 cell. Cells were treated with either soluble or aggregated (aged) Aβ1-42 in the presence or absence of AL04 for 3 days. Cell viability was assessed by WST-8 (water-soluble tetrazolium salt) reduction assay. * Soluble Aβ1-42, Aβ1-42 peptide in DPBS buffer; ** Aggregated Aβ1-42, aged Aβ1-42 solution for 3 days at 37° C.

Similar to undifferentiated PC12 cells, nerve growth factor (NGF)-treated (differentiated) PC12 cells showed about a 40% reduction of cellular viability when they were exposed to either soluble or aggregated Aβ1-42 treatment (10 µM) for 3 days. Apparently, 0.01 µM AL04 alone did not cause any harm in differentiated PC12 cells. Taken together, these data indicate that AL04 can protect cells against Aβ1-42-induced cytotoxicity (FIG. 7). It is evident that AL04 efficiently blocks Aβ aggregation, plaque formation, and neurotoxicity.

Example 10.5. Evaluation of BBB Permeability of AL04

In this study, we used a commercially available in vitro human BBB model purchased from Neuromics. We performed the BBB permeability assay by using concentrations from 1 to 10 µM. After the assay, we measured the concentration of AL04 from the brain side using human albumin quantitation ELISA and estimated the permeability coefficient ($P_e$) calculated by the formula described in Example 9. To confirm the fusion of TAT peptides in AL04 of the delivery platform (CysC-HSA-dTAT), the permeability through the BBB model of AL04 and non-TAT recombinant human serum albumin (rHSA) were compared. Several mechanisms have been proposed by which TAT protein disrupts BBB, including the decrease of tight junction protein expression, induction of vascular permeability in endothelium and relocalization (András, 2005; Xu, 2012; Zhong, 2012; Toschi, 2001).

As shown in FIG. 8A, dose-dependency results revealed that AL04 was transported across the model BBB. The dTAT containing AL04 tend to be transported into the brain side through the BBB model with higher permeability than rHSA. Also, we evaluated the effect of assay times on the permeability through the BBB model of the AL04 at 1 and 10 µM. We compared the permeability at three different assay times (60, 120, and 240 min). FIG. 8B showed that these $P_e$ did increase gradually until 120 min, but $P_e$ of 10 µM AL04 tends to slightly decrease at 240 min.

Example 11—Design for Dual Action Therapy Platform (Human Serum Albumin Fusion Protein)

Example 11.1—Materials and Methods

Figure 3:
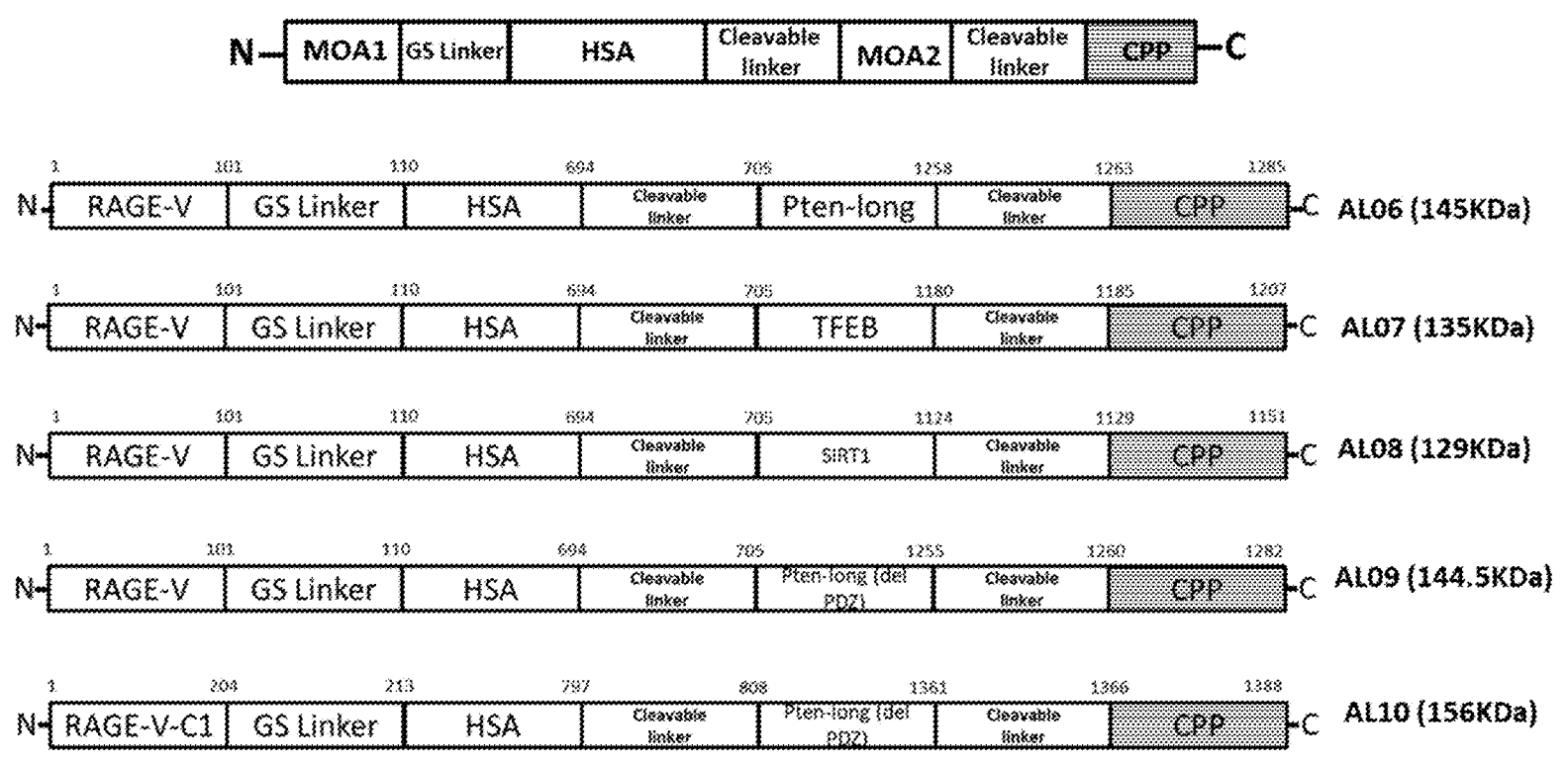
Figure 4:
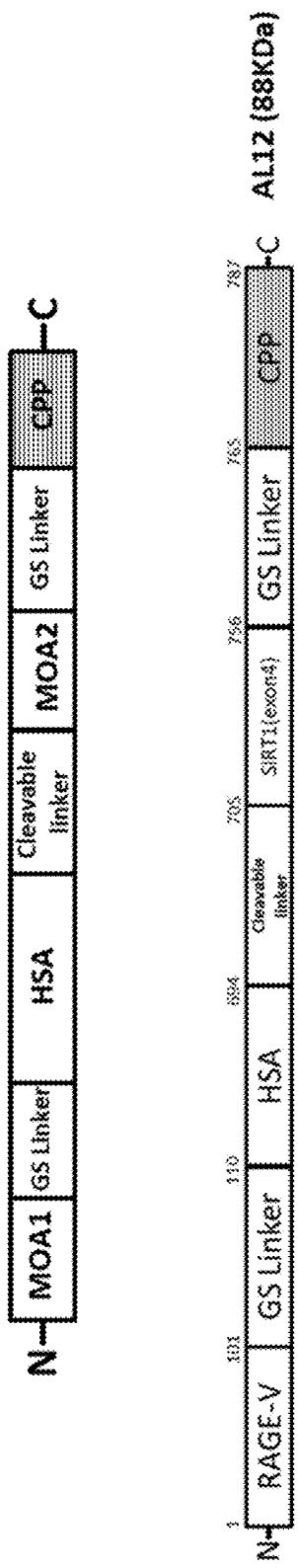
FIG. 4 shows schematic representation of HSA fusion protein (Version 2.1, AL12). The construct includes mechanism of action protein for lowering beta-amyloid plaque (MOA1) or Tau tangle (MOA2); GS linker (GGGSGGGS (SEQ ID NO:2)); human serum albumin (HSA); cleavable linker (GFLGGGGSAS (SEQ ID NO:4)); cell permeable peptide (CPP). Schematic illustration of AL12 (88 kDa) contains RAGE-V as MOA1; HSA as a carrier; SIRT1-exon4 as MOA2, and modified TAT peptide as CPP. The numbers on the boxes denote the amino acid numbers from the N-terminal of each HSA fusion protein.

In this study, Cystatin C sequences were chosen to test Version-1 HSA-fusion protein-CPP platform. To avoid the effect of bulky HSA structure on HSA-fusion protein platform Version1, a linker (GGSAS (SEQ ID NO:1)) was inserted between Cystatin C and HSA. A cleavable linker (GFLG) (SEQ ID NO:3) was inserted between HSA and CPP, it may facilitate liberation of CPP from HSA fusion protein penetration (FIG. 1). In HSA-fusion protein platform Version2 (MOA1-HSA-MOA2-CPP: AL06, AL07, AL08, AL09, AL10), four different protein sequences were chosen. V domain of receptor for advanced glycation end product (RAGE-V, RAGE-V&C1 domain for AL10) domain was used as a mechanism of action1 (MOA1) for reducing Abeta in Version-2. Three different proteins were used as a mechanism of action2 (MOA2) for charge of lowering phospho-Tau level: Pten-Long (for AL06), deleted PDZ domain of Pten-Long (for AL09&AL10); TFEB (Transcription factor EB, master regulator of the autophgy and lysosomal degradation) for AL07; SIRT1 (silent mating type information regulator 2 homolog 1, deacetylates Tau tangle and marks for proteosomal degradation) for AL08 respectively in version 2 platform. In version 2, various linkers were used: GS linker (GGGSGGGS (SEQ ID NO:2)) was inserted between MOA1 and HSA; GS linker/cleavable linker (GFLGGGG-SAS (SEQ ID NO:4)) was inserted between HSA and MOA2; cleavable linker (GFLG (SEQ ID NO:3)) was inserted between MOA2 and CPP (FIG. 3). For HSA-fusion protein platform Version2.1 (MOA1-HSA-MOA2-CPP: AL12), RAGE-V domain was used as a mechanism of action1 (MOA1) for reducing Abeta and 52 amino acids (exon 4 of SIRT1, a part of catalytic domain of SIRT1) was used as MOA2 for reducing phospho-Tau. In version 2.1, GS linker (GGGSGGGS (SEQ ID NO:2)) was inserted between MOA1 and HSA; between MOA2 and CPP. GS linker/cleavable linker (GFLGGGGSAS (SEQ ID NO:4)) was inserted between HSA and MOA2. We used various linkers to prevent steric hindrance between HSA and other fusion compartment (FIG. 4).

Example 12—Western Blot

PC12 cells were differentiated with 100 ng/ml NGF in 1% Horse serum containing DMEM media. After 4 days, NGF deprived PC12 cells were treated with various concentrations (0~10 ug/ml) of AL04 (or AL07, AL08, AL12) for 24 hr. The cells were rinsed twice in ice-cold DPBS (pH 7.5), lysed with lysis buffer and subjected to SDS-PAGE and immunoblot, as previously described (Bang, 2012). The following antibodies were used: Tau46 (total Tau), phospho-AMPKα (Thr 172), AMPKα, Phospho-AMPKβ (Ser182), AMPKβ, Phospho-ULK1 (Ser555), β3-tubulin, Cystatin C. GAPDH (glyceraldehyde-3-phosphate dehydrogenase) were from Cell Signaling Technology. phospho-Tau (AT8: Ser202/Thr205, Thermo), phospho-Tau (PHF-6: Thr231, Santa Cruz), anti-human albumin (Bethyl). SuperSignal West Pico chemiluminescence reagent (Thermo) was used for signal detection. Quantification of phospho-Tau and total Tau signals was performed by densitometry with ImageJ software (NIH). The phospho-Tau level at each time point was normalized to the total Tau level from the same sample and each normalized value was expressed as a percentage relative to the highest value, which was assigned 100%. Statistical significance was determined by Student's t test.

Example 13—Immunoprecipitation (IP)

Treated cells were lysed in 50 mM Tris (pH 7.4), 150 mM NaCl, 1% Triton X-100, 15% glycerol, phosphatase inhibitor cocktail (Santa Cruz), and protease inhibitor cocktail (BioVision). Total protein (1000 ug) was incubated with 5 µg β3-tubulin antibodies as indicated for 16 hours at 4° C. and precipitated with 60 µL TrueBlot anti-rabbit Ig immunoprecipitation beads (Rockland) for an additional 3 hours. Immunoprecipitated beads were washed 5 times with lysis buffer, and SDS-loading sample buffer was added. Samples were separated by SDS-PAGE and analyzed by immunoblotting as described before (Bang, 2014). For immunoprecipitates of Tau blots, Mouse TrueBlot ULTRA anti-mouse Ig horseradish peroxidase-conjugated secondary antibody (Rockland) was used for detection with SuperSignal West Pico chemiluminescence reagent (Thermo). Quantification of bound Tau and input Tau signals was performed by densitometry with ImageJ software (NIH). Statistical significance was determined by Student's t test.

Example 14—Results

Example 14.1—Characterization of Purified AL04 (80 kDa), AL07 (135 kDa), AL08 (129 kDa), and AL12 (88 kDa)

AL04 (Version1), AL07 and AL08 (Version2), and AL12 (Version2.1) were expressed and purified using blue dye affinity chromatography followed by ion-exchange column chromatography. The purified proteins were concentrated and buffer exchanged into PBS using ultrafiltration spin columns, and subsequently quantified using Bradford protein assay. AL04 and AL12 have over 90% purity seen in Coomassie blue-stain. Purity of AL07 and AL08 was confirmed by both coomassie stain and western blot, where a major band in coomassie staining gel match to that observed from western blot using human albumin antibody (FIGS. 5 and 11).

Example 14.2—Either AL04 or AL12 Penetrate into Differentiated PC12 Cells in Dose Dependent Manner While new strategies are consistently being evaluated to deliver functional proteins or peptides into cells, they are still lacking in overall efficiency and safety for translation into a clinical model (Zhang, 2012). Multiple modes of internalization have been shown to play a role, including receptor-mediated as well as endocytic pathways (Gradishar, 2005). Hence, we investigated whether AL04 or AL12 penetrate into cells. Cells were treated with various concentrations (0-5 ug/ml) of either AL04 or AL12 under NGF deprivation for 24 hours. Western blot analysis was employed to evaluate the extent of penetration of HSA fusion proteins into differentiated PC12 cells. As shown in FIG. 9, AL04 or AL12 proteins penetrate into differentiated PC12 cells in a dose dependent manner (FIG. 9). This indicates that different versions of HSA fusion proteins (AL04, Cystatin C-HSA-CPP; AL12, RAGE (V)-HSA-SIRT1 (exon4)-CPP) easily penetrate into PC12 cells and also could be effectively deliver their biological activity intracellularly.

Example 14.3—HSA-Fusion Proteins (AL04, AL07, and AL08) Affect Phosphorylation State of Tau in NGF-Deprived PC12 Cells AL07 and AL08 contain RAGE-V, which is a common Abeta reducing agent, and TFEB and SIRT1 as phospho-Tau lowering agents. Differentiated PC12 cells were treated with AL04 1 ug/ml, or 2 ug/ml of AL04, AL07, AL08, respectively for 24 hrs. Cells were lysed and total cell lysates (20 ug/lane) were separated by SDS-PAGE. Relative levels of Tau epitopes were determined by immunoblotting with the indicated antibodies: tau-46, a measure of total Tau; AT8, which recognizes the phosphorylated residues of Ser202/Thr205 on the Tau protein; PHF-6, which recognize the phosphorylated residues of Thr231 on the Tau protein. Administration of AL04, AL07, and AL08 resulted in decreased phosphorylation of Tau at Thr231, but only AL04 caused a decrease in p-Tau at Ser202/Thr205. Treatment with AL07 and AL08 failed to lower phosphorylation of Tau at Ser202/Thr205. Levels of total Tau, as measured by the Tau-46 antibody, were not changed by the AL04 treatment, but the levels of total Tau were slightly increased by AL07 and AL08 treatment. Results of immunoblot analysis provide evidence that the ratio of phospho-kinase to total Tau protein at Thr231, is decreased in AL04, AL07 or AL08 treatment (FIG. 12), whereas significant decrease in the ratio of phospho-kinase to total protein at Ser202/Thr205 from AL04 treatment is seen.

Example 14.4—AL04 Reduces NGF-Deprived Phospho-Tau Levels Through Down Regulation of I2PP2A (Inhibitor of PhosphotasePP2A)

Figure 13:
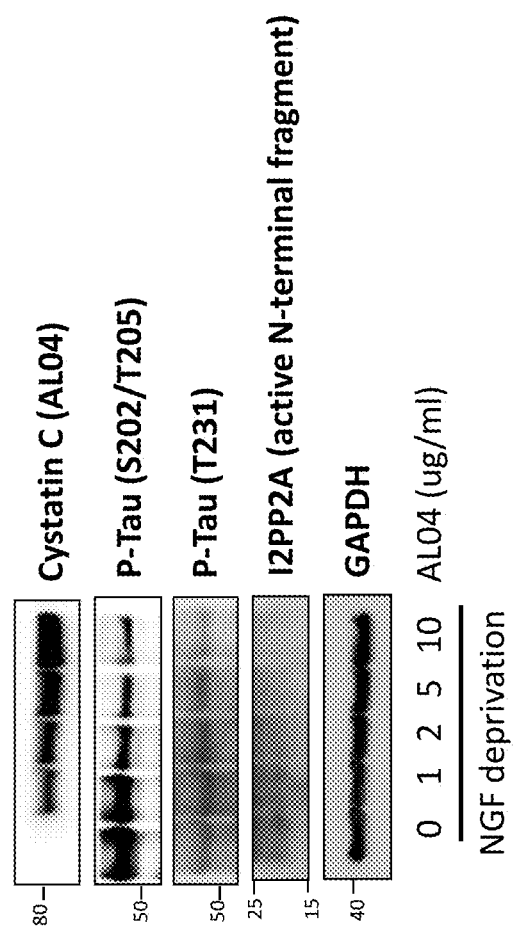
FIG. 13 shows that AL04 treatment reduces NGF-deprived phospho-Tau levels through down regulation of I2PP2A (inhibitor of phosphotase PP2A). PC12 cells were differentiated with 100 ng/ml NGF in 1% horse serum containing DMEM media. After 4 days, NGF deprived PC12 cells were treated with various concentrations (1-10 ug/ml) of AL04 for 24 hr. Cell lysates were subject to SDS-PAGE followed by Western blotting for Cystatin C (AL04), P-Tau (Ser202/Thr205), and I2PP2A. GAPDH was employed to confirm equal protein loading in the different lanes.

PP2A activity is compromised in AD and is believed to be a cause of the Tau neurofibrillary pathology. I2PP2A has been described as a potent inhibitor of PP2A, a phosphatase that accounts for ~70% of the adult human brain phosphoserine/phosphothreonine Tau protein phosphatase activity (Liu, 2005). Since Cystatin C is an inhibitor of AEP (Alvarez-Fernandez, 1999; van Kasteren, 2011), it might be possible that AL04 (harboring Cystatin C) affects regulation of PP2A activity involved with dephosphorylation of Tau through downregulation of I2PP2A. We therefore investigated whether AL04 treatment inhibits I2PP2A cleavage (activation). We treated differentiated PC12 cells for 24 hours with 1~10 ug/ml AL04 under NGF deprivation. As shown in FIG. 13, AL04 treatment decreased levels of ~20 kDa activated fragments of I2PP2A. We also observed AL04 treatment significantly reduced levels of P-Tau Ser202/Thr205 in dose dependent manner. Similarly, P-Tau Thr231 also showed slightly decreased levels in AL04 treated cells as compared to no treated cells. Levels of total Tau, as measured by the Tau-46 antibody, were not changed by the AL04 treatment. No changes in GAPDH were observed. These results suggested that AL04 reduces NGF deprivation-induced hyperphosphorylation of Tau levels due to rescue PP2A activity through down regulation of I2PP2A.

Example 14.5—Effects of Lowering Tau Phosphorylation on Tubulin-Tau Interaction

Tau plays an important role in regulating microtubule dynamics in neuronal development. It has been shown that phosphorylation of key sites on Tau has a strong impact on the normal function of Tau and likely contributes to its pathological role (Cho, 2004; Sengupta, 1998; Lin, 2007). We next investigated whether NGF deprivation-induced hyper-phosphorylation of Tau would be necessary to affect tubulin binding by testing in the presence or absence of AL04. We observed that treatment of AL04 increased Tautubulin binding level 2-fold relative to the level obtained with no treatment (FIG. 14), indicating that AL04 restores reduced microtubule-Tau interaction by NGF deprivation through reducing phospho-Tau level.

Figure 15:
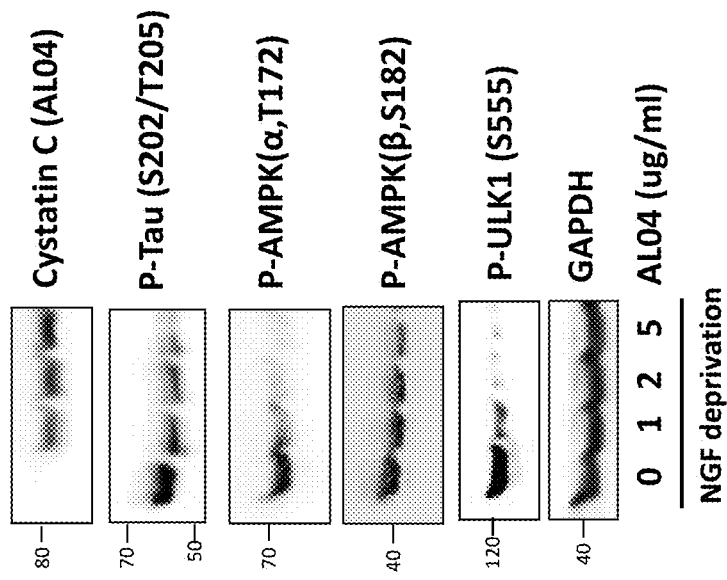
FIG. 15 shows AL04 reduces hyperphospho-Tau via modulating AMPK in dose-dependent manner. Representative blots of Cystatin C (AL04), phospho-Tau (Ser202/Thr205), phospho-AMPKalpha (Thr172), phospho-AMPK-beta (Ser182), phospho-ULK1 (Ser555), upon treatment of NGF deprived PC12 cells with various concentrations (1-5 ug/ml) of AL04 for 24 hrs is shown. GAPDH was used as loading control.

Example 14.6—AL04 Reduces Hyperphospho-Tau Via Modulating Tau Kinases (AMPK) in Dose-Dependent Manner Since AL04 treatment reduces phospho-Tau, we tested whether AL04 treatments also altered activation of several kinases potentially involved with phosphorylation of Tau. Endogenous AMPK activation in AD brain and mouse primary neurons induced an increase of Tau phosphorylation at multiple sites, where AMPK inhibition led to a rapid decrease of Tau phosphorylation (Vingtdeux, 2011; Domise, 2016). Accordingly, we investigated the possibility that AL04 caused reduction of NGF deprivation-induced hyperphospho-Tau and AMPK signal pathway are related. Because AMPK activation requires the phosphorylation of Thr172 in the activation loop of α1 and α2 subunits, AMPK activity was determined by Western blots detecting the expression levels of phospho-AMPK (Bang. 2012; Bang 2014). We performed the following experiments. First, an antibody against AMPK activated catalytic a subunit, p-AMPK (Thr172) and regulatory subunit, β1 was used to conduct Western blotting. As shown in FIG. 15, reduced levels for p-AMPK (Thr172) and p-AMPKβ 1 (Ser182) observed in dose dependent manner, suggesting AL04 treatment reduced AMPK activity. Second, we examined ULK1, AMPK dependent substrate and a regulator of autophagy (Egan, 2011; Kim, 2011; Guha, 2019), and observed highly decreased phosphorylation of ULK1 on Ser 555 in an AMPK-dependent manner after treatment of cells with AL04. Notably, the reduced p-ULK1 (Ser555) levels in these cells paralleled that of two bona-fide AMPK substrates, ACC and Raptor (data not shown). GAPDH was unchanged. It suggested that AL04 treatment may modulate (inactivate) AMPK, known to be Tau kinase, it contributes to lower phospho-Tau level in PC12 cells.

Example 15—Description of Hippocampus and Entorhinal Experiment Using Tg2576, JNPL3 Mice In human AD, memory deficits associated with disease progression are likely to result from pathological changes in the entorhinal cortex (EC) and hippocampus, regions critical for formation of new memories and among the most vulnerably affected in AD (Knowles, 1998; Alvarez, 1995; Bannerman, 2001; Buckmaster, 2004). The hippocampus is comprised of subfields: dentate gyrus (DG), CA1, CA2, CA3, and subiculum. It has been reported that hippocampus and EC are primary sites for Aβ deposition in Tg2576 mice, which overexpress human APP with the Swedish double mutations (K670N, M671L) (Hsiao, 1996; Su, 1998; Reilly, 2003; Dong. 2007; Lauritzen, 2012; Xu, 2015) and also exhibiting pathological Tau (neurofibirillary tangles containing oligomeric/aggregated phospho-Tau) in JNPL3 mice, which express human Tau with the P301L mutation (Lewis, 2000; Lin, 2003; Acker, 2013; Vitale, 2018). To evaluate the efficacy of AL04 against Alzheimer's disease (AD), we investigated whether AL04 could decrease burden of amyloid beta (Aβ) and/or hyperphosphorylated Tau in the hippocampus and EC of Tg2576 and JNPL3 mice, respectively. The changes in Aβ deposition or hyperphosphorylated Tau by treatment with AL04 are compared to control (PBS injected) animal using immunohistochemistry assay.

Example 15.1—Animals and Treatment

The 9~10-month-old Tg2576 female mice and 3~4-month-old JNPL3 mice used in the present study were purchased from Taconic Farms (Germantown, NY, USA) and were maintained and handled in accordance with a protocol approved by the Institutional Animal Care and Use Committee of Noble Life Science, Inc. (Sykesville, MD, USA) (Approval no. NLS-511). All animal experiments in the present study were planned by L&J Biosciences, Inc. and conducted with Noble Life Science, Inc. Tg2576 mice were treated with either 10 mg/kg of AL04 or PBS by intraperitoneal injections weekly during 2 months. JNPL3 mice were treated with either 5 mg/kg of AL04 or PBS by intraperitoneal injections bi-weekly during 6 months. After treatment animals were anaesthetized with isoflurane and brains were removed. The brain was divided at the midline (sagittal) so that just one half of the brain was dissected for immunohistochemistry analysis.

Example 15.2—Histology and Immunohistochemistry Analysis

Brains were post-fixed another 24 hours and then embedded in paraffin using standard protocols. Coronal sections (5 μm) were cut on a microtome and processed for immunohistochemistry using the following primary antibodies: 6E10 (residues 1-16 of human Aβ, Biolegend, 1:500), AT8 (phospho-Tau Ser202/Thr205, Thermo, 1:1000) and HT7 (Total Tau, Thermo, 1:1000). After incubation with the primary antibodies, sections were washed in PBS and then sections were incubated with secondary antibodies (HRP-conjugated (1:1000, Jackson Labs) or fluorescent AlexaFluor antibodies, Alexa 488-conjugated (Thermo, 1:1000)). For detecting Aβ deposition in Tg2576 mice brain sample or total Tau in JNPL3 mice brain, slides with HRP-conjugated antibodies were incubated with Diaminobenzidine (DAB), rinsed and counter-stained with hematoxylin. For DAB development, slides were analyzed using an optical light microscope (Zeiss). Fluorescent slides were incubated for 5 minutes with DAPI for stained nuclei. Immunofluorescence of phospho-Tau in JNPL3 mice brain sample was visualized using a confocal microscope (Zen2, Zeiss) with excitation filters 340 (for DAPI, blue) and 488 (for p-Tau, green). Histology/Immunohistochemistry and Imaging procedures were planned by L&J Biosciences Inc., conducted by Histoserve (Germantown, MD, USA) and CVPath (Gaithersburg, MD, USA), respectively.

Example 16—Results

Figure 16:
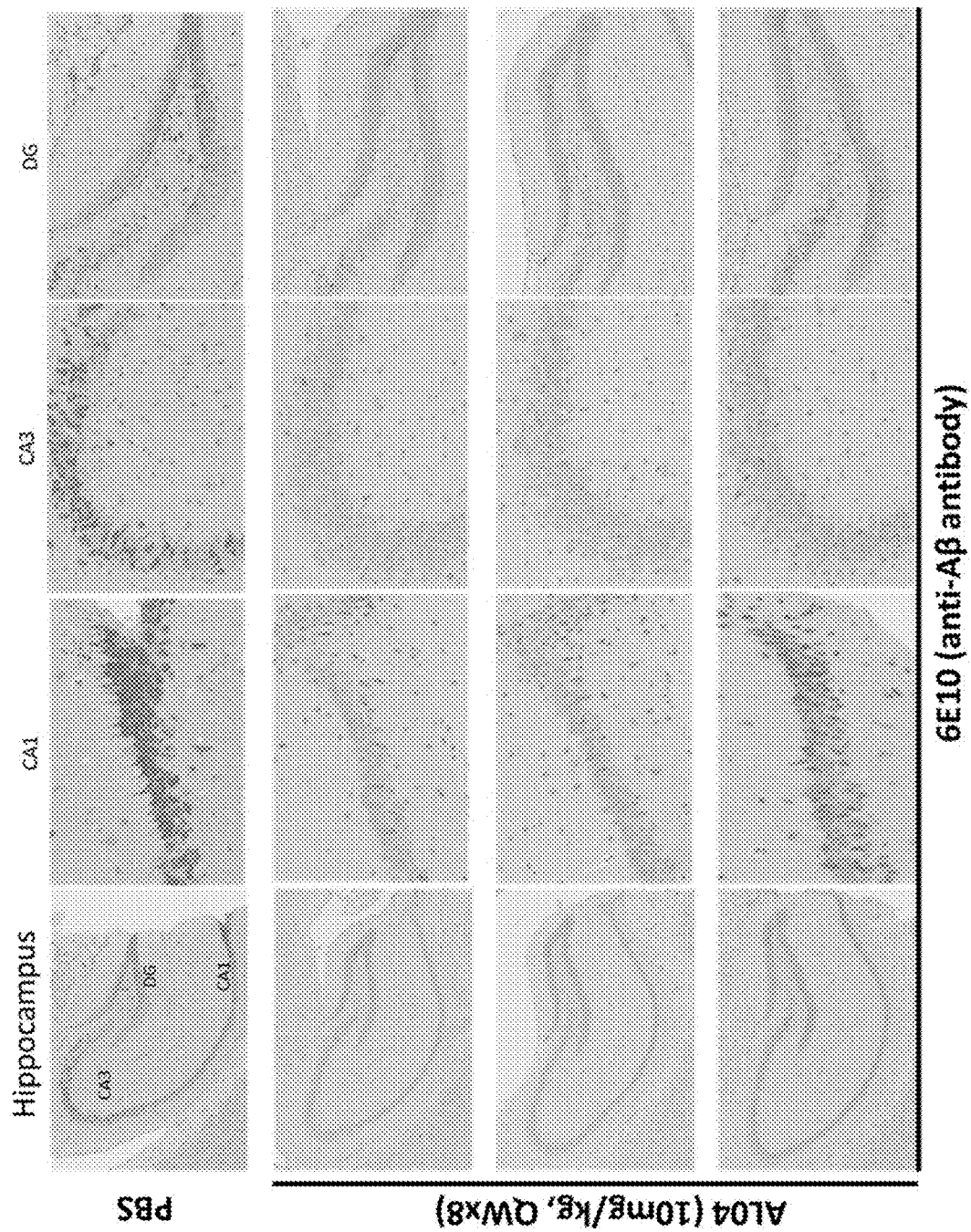
FIG. 16 shows that treatment with AL04 decreases amyloid beta (Abeta) deposition in the hippocampus of Tg2576 mouse.
Figure 17:
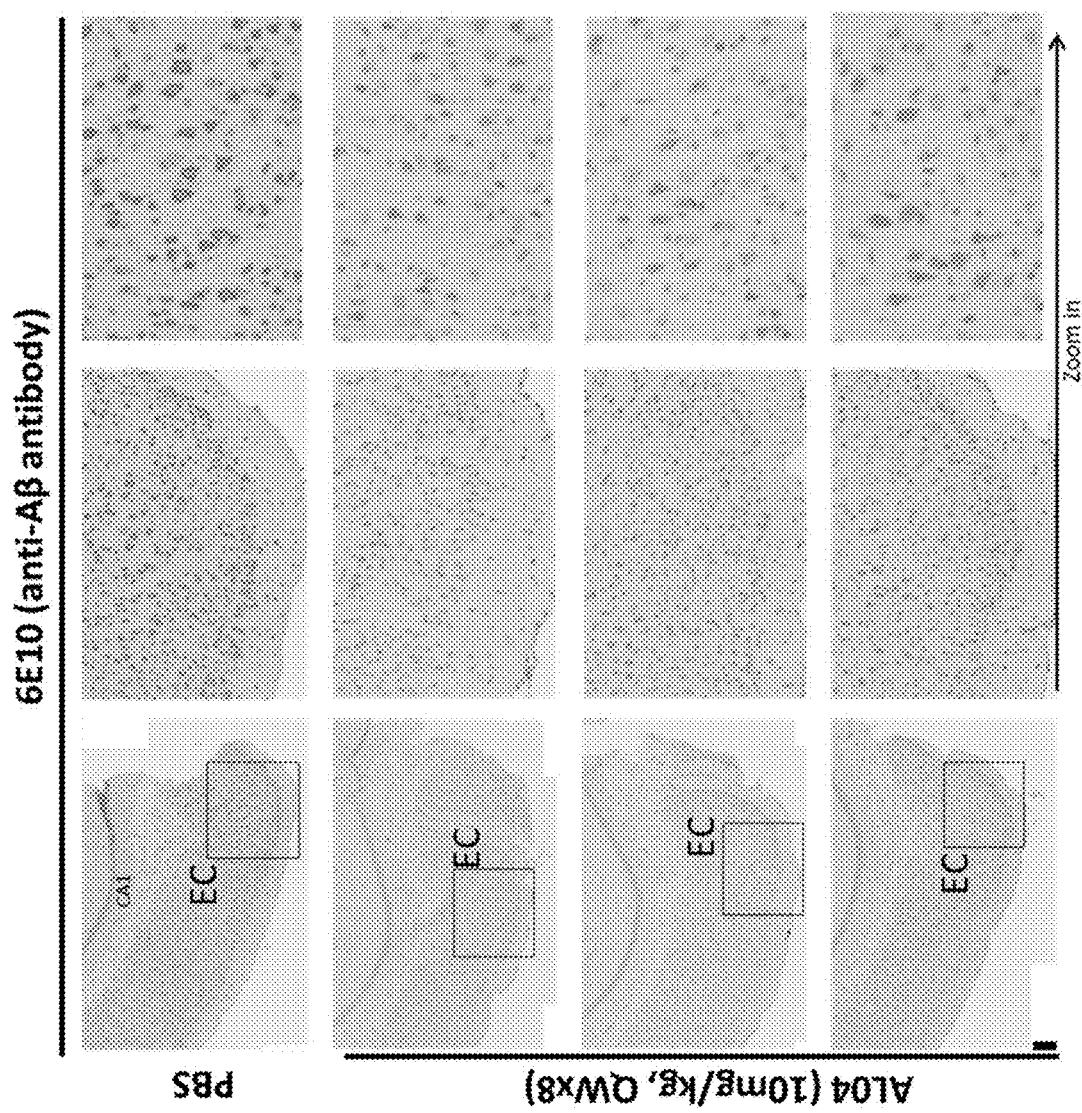
FIG. 17 shows that treatment with AL04 decreases amyloid beta (Abeta) deposition in the entorhinal cortex of Tg2576 mouse.

Example 16.1—AL04 Decreases Deposition of Amyloid Beta in Hippocampus and Entorhinal Cortex of Tg2576 Mice Based on the amyloid cascade hypothesis, the accumulation and aggregation of Aβ triggers pathological and clinical symptoms of AD development (Walsh, 2012; Hardy, 1992; Hardy, 2002). Previous studies have reported that Aβ accumulation occurred in the brain of Tg2576 mice and developed behavioral impairment (Hsiao, 1996). It has been known that the changes of perforant pathway, which are neuronal projections from the entorhinal cortex to dentate gyrus of hippocampus, are associated with memory impairment (Hyman, 1984; Hyman, 1986; Gomez-Isla, 1996; van Strien, 2009). Hence, we investigated whether AL04 treatment reduced Aβ accumulation in the hippocampus and entorhinal cortex of Tg2576 mice. Starting at 9~10 months of age, Tg2576 mice received weekly intraperitoneal injections of either PBS or AL04 (10 mg/kg). Animals received a total of 8 doses and were killed at 9 weeks. The AL04 treatment was well tolerated. Amyloid β precursor protein (AβPP) is processed by α- and β-secretases. The 6E10 antibody recognizes the first 16 residues of the Aβ domain and therefore theoretically labels full-length βAPP, C99 (15 KDa of APP fragment by digested with beta-secretase, BACE1) and Aβ (Lauritzen, 2012). In 11~12 month-old of PBS-treated Tg2576 mice, 6E10 (FIG. 16) shows the presence of dense deposition (brown color) in the hippocampus at the area of the CA1, CA3, and DG subfields. Also, in the entorhinal cortex of PBS-treated animals, 6E10 labels strongly indicating extracellular Aβ deposition (FIG. 17). In contrast, there is shown to be reduced Aβ accumulation in each subfield of hippocampus (CA1, CA3, and DG) and entorhinal cortex of AL04-treated Tg2576 mice (FIGS. 16 and 17). These results indicate that AL04 decreases Aβ burden in hippocampus and entorhinal cortex of human APP mutant harboring Tg2576 mice.

Example 16.2—AL04 Reduces Hyperphosphorylated Tau in Hippocampus of JNPL3 Mice

In AD and other neurodegenerative disorders, Tau is hyper-phosphorylated and disassociated from microtubules, resulting in phospho-Tau aggregation and the formation of neurofibrillary tangles in neuronal somata and dendrites. These neurofibrillary tangles (NFT) are well recognized by multiple phospho-Tau on serine and threonine antibodies/paired helical filament (PHF) such as AT8 (p-TauS202/T205), AT100, and PHF1 (p-TauS396/404) (Lewis, 2000; Augustinack, 2002; Lace, 2009).

NFT formation is closely associated with pathological symptoms in tauopathy models (Braak, 1991, 1997; Duyckaerts, 1997; Rub, 2000; Sassin, 2000; Lewis, 2000; Lacc, 2009). JNPL3 mice, which express human Tau P301L mutation that causes frontotemporal dementia in humans, develop NFTs as early as 4.5 months and in later stages progressive deterioration of the motor function (Lewis, 2000). We investigated whether AL04 treatment could reduce the level of phospho-Tau in the hippocampus and EC of JNPL3 mice. Starting at 3~4 months of age, JNPL3 mice received bi-weekly intraperitoneal injections of either PBS or AL04 (5 mg/kg) for 6 months. Animals received a total of 12 doses and were killed at 25 weeks.

As a proof of concept of lowering the level of hyperphosphorylated Tau, AT8 (Phospho-Tau, S202/T205) immunofluorescence analysis was performed in the CA1/CA3 through DG subfield of the hippocampus and EC. Hippocampus and EC, perforant pathway, are play a major role in memory formation and are vulnerable region in Tau pathology, dementia, and mild cognitive impairment relatively early in aging (Braak and Braak, 1991; Duyckaerts, 1997; Tulving, 1998; Braak, 2006; Lace, 2009).

Figure 18:
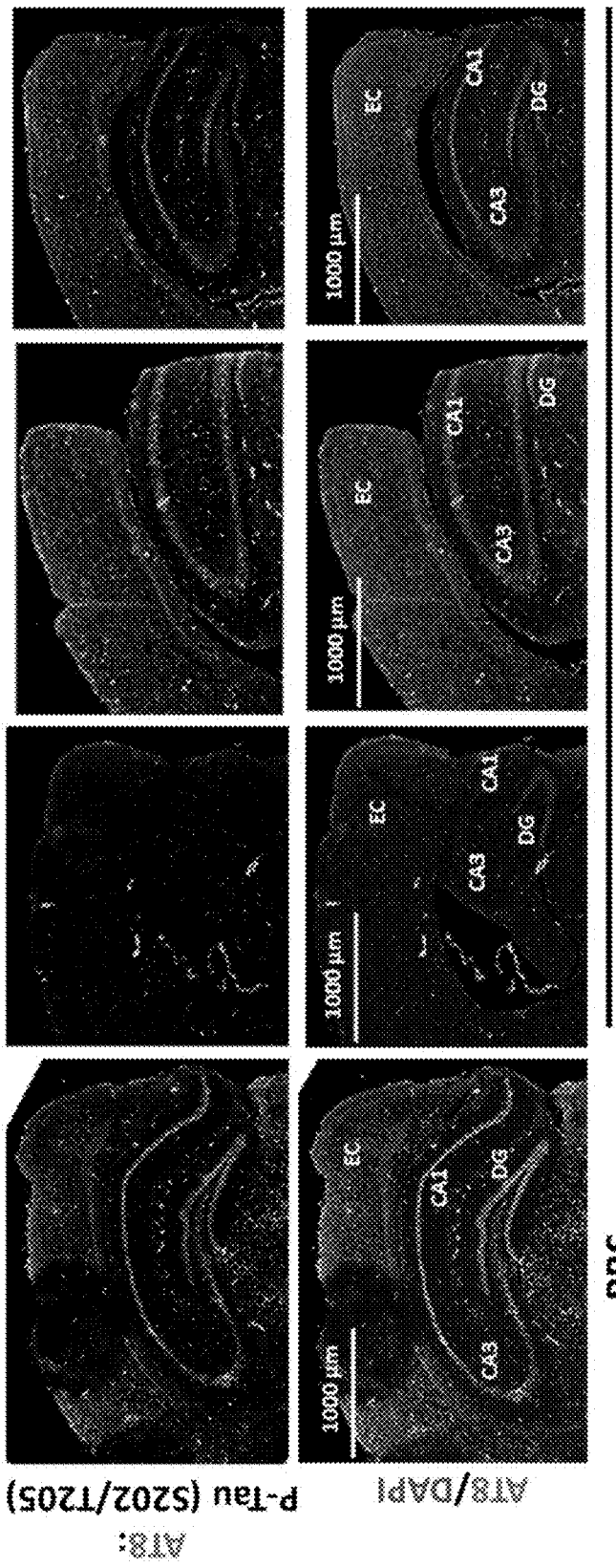
FIG. 18 shows that treatment with AL04 reduces level of hyperphosphorylated Tau in the hippocampus and entorhinal cortex of JNPL3 mouse.

We observed phosphor-Tau (S202/T205) positive cells in the hippocampus of PBS-treated 9~10 month old animal (FIG. 18). The presence of phosphor-Tau (S202/T205) suggests that axonal Tau is abnormally phosphorylated and raises the possibility that axonal dysfunction in projections to the hippocampus is a common, early change in ageing (Lace, 2009). In contrast, a significant reduction of phosphor-Tau levels (S202/T205) was detected in the CA1 and CA3 subfield of hippocampus and EC of AL04 treated 9~10 months old mice (FIG. 18). These results suggested that AL04 lowers NFTs (hyper-phosphorylated Tau) in the hippocampus and EC of JNPL3 mice and also attenuates spread of Tau pathological severity within subfields of the hippocampus containing CA1, CA3, and dentate gyrus.

Cystatin C plays a neuroprotective role in AD development and has clinical relevance as therapeutic agent (Li, 1996; Tizon, 2010). Investigation of the choice of carrier and/or CPP for Cystatin C containing dual action therapy (DAT) platform as candidates of AD therapeutics is summarized in FIG. 10. Four variant constructs of AL04, named AL04-1 to AL04-4, which contain Fc or HSA as carrier protein (also known as long-lasting protein in vivo) and dNP2 (Lim, 2015) or dTAT as CPP were made as described in Example 11.1. By using these constructs, protein expression was tested in either CHO-S cells or CHO-DG44 cells for transient and stable expression respectively (data not shown). Either Fc or HSA with dTAT as CPP containing construct showed greater protein expression level than those constructs with dNP2. Moreover, HSA fusion with dTAT was observed to have better expression in both transient and stable expression than Fc fusion construct (data not shown). Undesirable immune cell activation was reported in that Fc-fusion protein induced inflammatory cytokine release from human PBMC (Edwards, 2014). It is suggested that CysC-HSA-dTAT is a suitable construct of DAT platform for the development of AD therapeutics. The DAT platform was applied to the establishment of seven different constructs, which are candidates of therapeutics for AD treatment (versions 1 and 2), and summary of their expression and purification are shown in FIG. 11. Seven different constructs were prepared as described in Example 11.1 and their expression and process of purification were studied. The level of fusion protein expression including transient expression and gene amplification using MTX in DHFR deficient CHO-DG44 cells determined by Western blot or Coomassie staining (data not shown), was dependent on molecular weight. AL06 (145 kDa), AL09 (144.5 kDa), and AL10 (156 kDa) barely expressed the proteins and failed to produce protein through MTX/DHFR gene amplification method. To determine the quality of each fusion protein, proteins were purified as described in Example 5 and analyzed by SDS-PAGE (data not shown). AL07 and AL08 proteins were partially purified because these proteins were degraded during purification (FIG. 5). FIG. 11 shows that AL04 (80 kDa) and AL12 (88 kDa) are good constructs for protein expression and purification.

REFERENCES

Acker et al., Sensitive quantitative assays for tau and phospho-tau in transgenic mouse models. Neurobiol Aging. 2013; 34 (1): 338-350.

Alvarez P. Zola-Morgan S, Squire L R. Damage limited to the hippocampal region produces long-lasting memory impairment in monkeys. J Neurosci. 1995; 15:3796-807.

Alvarez-Fernandez et al., Inhibition of Mammalian Legumain by some Cystatins is due to a novel second reactive site. J. Biol. Chem. 1999; 274 (27), 19195-19203.

Amy C M, Bennett E L. Increased sodium ion conductance through nicotinic acetylcholine receptor channels in P C12 cells exposed to nerve growth factors. J Neurosci 1983; 3:1547-1553.

Andersen J T. Dalhus B, Viuff D, et al. Extending serum half-life of albumin by engineering neonatal Fc receptor (FcRn) binding. J Biol Chem. 2014; 289:13492-13502.

András et al. Signaling mechanisms of HIV-1 TAT-induced alterations of claudin-5 expression in brain endothelial cells. J. Cereb. Blood Flow Metab. 2005; 25:1159-1170.

Arnaud et al., Mechanism of inhibition of PP2A activity and abnormal hyperphosphorylation of Tau by I2PP2A/SET. FEBS Lett. 2011; 585, 2653-2659.

Arriagada et al., Neurofibrillary tangles but not senile plaques parallel duration and severity of Alzheimer's disease. Neurology 1992; 42 (3 Pt 1): 631-9.

Augustinack et al., Specific tau phosphorylation sites correlate with severity of neuronal cytopathology in Alzheimer's disease. Acta Neuropathol 2002; 103:26-35.

Ballatore et al., Tau-mediated neurodegeneration in Alzheimer's disease and related disorders. Nat Rev Neurosci. 2007; 8:663-672.

Bang S, Kim S, Dailey M J, et al. AMP-activated protein kinase is physiologically regulated by inositol polyphosphate multikinase. Proc Natl Acad Sci USA. 2012; 109 (2): 616-620.

Bang S, Chen Y, Ahima R S, and Kim S F. Convergence of IPMK and LKB1-AMPK signaling pathways on metformin action. Mol. Endocrinol. 2014; 28:1186-1193.

Banks W A et al, Permeability of the blood-brain barrier to HIV-1 TAT. Exp. Neurol. 2005; 193:218-227.

Banks W A. Drug delivery to the brain in Alzheimer's disease: consideration of the blood-brain barrier. Adv. Drug Deliv. Rev. 2012; 64 (7): 629-639.

Banks W A. From blood-brain barrier to blood-brain interface: new opportunities for CNS drug delivery. Nature Reviews Drug Discovery 2016; 15:275-292.

Bannerman et al., The role of the entorhinal cortex in two forms of spatial learning and memory. Exp Brain Res. 2001; 141:281-303.

Basurto-Islas et al., Activation of asparaginyl endopeptidase leads to Tau hyperphosphorylation in Alzheimer disease. J Biol Chem. 2013 Jun. 14; 288 (24): 17495-507.

Boado, R J, Zhang, Y F, Zhang, Y, Xia, C F, Pardridge, W M. Fusion antibody for Alzheimer's disease with bidirectional transport across the blood-brain barrier and abeta fibril disaggregation. Bioconjug Chem 2007; 18:447-455.

Boado, R J, Zhang, Y, Xia, C F, Wang, Y, Pardridge, W M. Genetic engineering of a lysosomal enzyme fusion protein for targeted delivery across the human blood-brain barrier. Biotechnol Bioeng 2008; 99:475-484.

Boado R J, Zhou Q H, Lu J Z, Hui E K, Pardridge W M. Pharmacokinetics and brain uptake of a genetically engineered bifunctional fusion antibody targeting the mouse transferrin receptor. Molecular pharmaceutics. 2009; 7:237-244.

Boado R J, Hui E K-W, Lu J Z, Sumbria R K, Pardridge W M. Blood-brain barrier molecular trojan horse enables imaging of brain uptake of radioiodinated recombinant protein in the rhesus monkey. Bioconjug Chem 2013; 24:1741-9.

Braak H and Braak E. Diagnostic criteria for neuropathologic assessment of Alzheimer's disease. Neurobiol Aging 1997; 18: S85-8.

Braak H and Braak E. Neuropathological stageing of Alzheimer-related changes. Acta Neuropathol. 1991; 82:239-259.

Braak H and Braak E. Staging of Alzheimer's disease-related neurofibrillary changes. Neurobiol Aging 1995; 16:271-8. 278-84.

Braak H, Rub U, Schultz C, Del Tredici K. Vulnerability of cortical neurons to Alzheimer's and Parkinsons's Diseases. J Alzheimers Dis 2006; 9:35-44.

Bramblett et al., Abnormal tau phosphorylation at Ser396 in Alzheimer's disease recapitulates development and contributes to reduced microtubule binding. Neuron. 1993; 10:1089-1099.

Brandt, R., Leger, J. & Lee, G. Interaction of tau with the neural plasma membrane mediated by tau's amino-terminal projection domain. J. Cell Biol. 1995; 131, 1327-1340

Brewster M E, Anderson W R, Webb Al, et al., Evaluation of a brain-targeting zidovudine chemical delivery system in dogs. Antimicrob. Agents Chemother., 1997, 41, 122.

Buckmaster et al., Entorhinal cortex lesions disrupt the relational organization of memory in monkeys. J Neurosci. 2004; 24:9811-25.

Cao et al., In vivo delivery of a Bcl-xL fusion protein containing the TAT protein transduction domain protects against ischemic brain injury and neuronal apoptosis. J. Neurosci. 2002; 22:5423-5431.

Chang R. Knox J, Chang J, Derbedrossian A, Vasilevko V, Cribbs D, et al. Blood-brain barrier penetrating biologic TNF-alpha inhibitor for Alzheimer's disease. Mol Pharm. 2017; 14 (7): 2340-9.

Chaudhury, C., Mehnaz, S., Robinson, J. M., Hayton, W. L., Pearl, D. K., Roopenian, D. C., and Anderson, C. L. The major histocompatibility complex-related Fc receptor for IgG (FcRn) binds albumin and prolongs its lifespan. J. Exp. Med. 2003; 197:315-322.

Carelli, V., Liberatore, F., Scipione, L., Impicciatore, M., Barocelli, E., Cardellini, M. an d Giorgioni, G. New system for the specific delivery and sustained release of dopamine to the brain. J. Controlled Release, 1996; 42:209-216

Cho, J.-H. & Johnson, G. V. W. Primed phosphorylation of tau at Thr 231 by glycogen synthase kinase 3B (GSK3β) plays a critical role in regulating tau's ability to bind and stabilize microtubules. J. Neurochem. 2004; 88:349-358.

Chung S H. Aberrant phosphorylation in the pathogenesis of Alzheimer's disease. BMB Rep 2009; 42:467-74.

Domise et al., AMP-activated protein kinase modulates tau phosphorylation and tau pathology in vivo. Sci. Rep. 2016; 6:26758.

Dong et al., Spatial Relationship Between Synapse Loss and β-Amyloid Deposition in Tg2576 Mice. J Comp Neurol. 2007; 500 (2): 311-321.

Drubin, D., Feinstein, S. C., Shooter, E. M. & Kirschner, M. Nerve growth factor induced neurite outgrowth in PC12 cells involves the coordinate induction of microtubule assembly and assembly-promoting factors. J. Cell Biol. 1985; 101:1790-1807.

Duyckaerts C and Hauw J J. Prevalence, incidence and duration of Braak's stages in the general population: can we know? Neurobiol Aging 1997; 18:362-9.

Edwards W, Fung-Leung W P, Huang C, Chi E, Wu N, Liu Y, et al. Targeting the Ion Channel Kv1.3 with Scorpion Venom Peptides Engineered for Potency, Selectivity, and Half-life. J. Biol. Chem. 2014; 289:22704-22714.

Egan et al. Phosphorylation of ULK1 (hATG1) by AMP-activated protein kinase connects energy sensing to mitophagy. Science 2011; 331:456-461.

Gabathuler R. Approaches to transport therapeutic drugs across the blood-brain barrier to treat brain diseases. Neurobiol. Dis. 2010; 37:48-57.

Goedert M. Tau protein and the neurofibrillary pathology of Alzheimer's disease. Trends Neurosci 1993; 16:460-5.

Gómez-Isla T, Price J L, McKeel D W, Morris J C, Growdon J H, Hyman B T. Profound loss of layer II entorhinal cortex neurons occurs in very mild Alzheimer's disease. J Neurosci 1996; 16:4491-4500.

Gradishar et al., Phase III trial of nanoparticle albumin-bound paclitaxel compared with polyethylated castor oil-based paclitaxel in women with breast cancer. J Clin Oncol 2005; 23:7794-7803.

Grundke-Iqbal et al., Abnormal phosphorylation of the microtubule-associated protein tau (tau) in Alzheimer cytoskeletal pathology. Proc Natl Acad Sci USA. 1986; 83:4913-4917.

Guha P, Tyagi R, Chowdhury S, Reilly L, Fu C, Xu R, Resnick A C, and Snyder S H. IPMK Mediates Activation of ULK Signaling and Transcriptional Regulation of Autophagy Linked to Liver Inflammation and Regeneration. Cell Rep. 2019; 26 (10): 2692-2703.

Gynther M, Laine K, Ropponen J, et al. Large neutral amino acid transporter enables brain drug delivery via prodrug. J. Med. Chem. 2008; 51:932-936.

Gynther M, Ropponen J, Laine K, Leppänen J, Haapakoski P, Peura L, et al. Glucose promoiety enables glucose transporter mediated brain uptake of ketoprofen and indomethacin prodrugs in rats. J Med Chem. 2009; 52 (10): 3348-53.

Hanemaaijer R, Ginzburg I. Involvement of mature tau isoforms in the stabilization of neurites in PC12 cells. J Neurosci Res. 1991; 30:163-171.

Hardie D G. AMP-activated protein kinase: an enrgy sensor that regulates all aspects of cell function. Genes dev. 2011; 25 (18): 1895-908.

Hardy J, and Selkoe D J. The amyloid hypothesis of Alzheimer's disease: progress and problems on the road to therapeutics. Science. 2002; 297:353-356.

Hardy J A, and Higgins G A. Alzheimer's disease: the amyloid cascade hypothesis. Science. 1992; 256:184-185.

Hensley K, Carney J M, Mattson M P, Aksenova M, Harris M, Wu J F, Floyd R A, Butterfield D A. A model for beta amyloid aggregation and neurotoxicity based on free radical generation by the peptide: relevance to Alzheimer disease. Proc Natl Acad Sci USA 1994; 91:3270-3274.

Hsiao et al., Correlative memory deficits, Abeta elevation, and amyloid plaques in transgenic mice. Science 1996, 274:99-102.

Hyman B T, van Hoesen G W. Damasio A R, Barnes C L. Alzheimer's disease: cell-specific pathology isolates the hippocampal formation. Science 1984; 25:1168-1170.

Hyman et al., Perforant pathway changes and the memory impairment of Alzheimer's disease. Ann Neurol, 1986; 20:472-481.

Ishihara T et al., Age-dependent emergence and progression of a tauopathy in transgenic mice overexpressing the shortest human tau isoform. Neuron. 1999; 24:751-762.

Jumblatt J E, Tischler A S. Regulation of muscarinic ligand binding sites by nerve growth factor in PC12 phaeochromocytoma cells. Nature 1982; 297:152-154.

Juszczyk, P., Paraschiv, G., Szymanska, A., Kolodziejczyk, A. S., Rodziewicz-Motowidlo, S., Grzonka, Z., and Przybylski, M. Binding epitopes and interaction structure of the neuroprotective protease inhibitor cystatin C with β-amyloid revealed by proteolytic excision mass spectrometry and molecular docking simulation. J. Med. Chem. 2009; 52. 2420-2428.

Kang et al., Donepezil, tacrine and alpha-phenyl-n-tert-butyl nitron (PBM) inhibit choline transport by conditionally immortalized rat brain endothelial cell lines (TR-BBB) Archives of Pharmacal Research. 2005; 28:443-450.

Kilic et al., Intravenous TAT-Bcl-Xl is protective after middle cerebral artery occlusion in mice. Ann. Neurol. 2002; 52:617-622.

Kim et al., Evidence of carrier-mediated transport in the penetration of donepezil into the rat brain. Journal of Pharmaceutical Sciences. 2010; 99:1548-1566.

Kim J, Kundu M, Viollet B, and Guan K L. AMPK and mTOR regulate autophagy through direct phosphorylation of Ulk1. Nat. Cell Biol 2011; 13:132-141.

Knowles et al., Abeta associated neuropil changes: correlation with neuronal loss and dementia. J Neuropathol Exp Neurol. 1998; 57:1122-30.

Kosik et al., Microtubule-associated protein tau (tau) is a major antigenic component of paired helical filaments in Alzheimer disease. Proc Natl Acad Sci USA. 1986; 83:4044-4048.

Ksiezak-Reding et al., Phosphate analysis and dephosphorylation of modified tau associated with paired helical filaments. Brain Res 1992; 597:209-19.

Lace et al., Hippocampal tau pathology is related to neuroanatomical connections: an ageing population-based study. Brain. 2009; 132:1324-1334.

Lauritzen I, Pardossi-Piquard R, Bauer C, Brigham E, Abraham J D, Ranaldi S, Fraser P, St-George-Hyslop P, Le Thuc O, Espin V, Chami L, Dunys J, and Checler F. The β-secretase derived C-terminal fragment of βAPP, C99, but not Aβ, is a key contributor to early intraneuronal lesions in triple transgenic mouse hippocampus. J Neurosci. 2012 Nov. 14; 32 (46): 16243.

Lee et al., A68: a major subunit of paired helical filaments and derivatized forms of normal Tau. Science. 1991; 251:675-678.

Lee V M, Goedert M, Trojanowski J Q. Neurodegenerative tauopathies. Annu Rev Neurosci. 2001; 24:1121-1159.

Lewis et al., Neurofibrillary tangles, amyotrophy and progressive motor disturbance in mice expressing mutant (P301L) tau protein. Nat Genet. 2000; 25 (4): 402-405.

Li et al., The myeloid leukemia-associated protein SET is a potent inhibitor of protein phosphatase 2A. J. Biol. Chem. 1996; 271, 11059-11062.

Liao et al., Degradation of Amyloid beta Protein by Purified Myelin Basic Protein. J. Biol. Chem. 2009; 284:28917-28925.

Lim S, Kim W J, Kim Y H, Lee S, Koo J H, Lee J A, et al. dNP2 is a blood-brain barrier-permeable peptide enabling ctCTLA-4 protein delivery to ameliorate experimental autoimmune encephalomyelitis. Nature communications. 2015; 6:8244.

Lin Y T, Cheng J T, Liang L C, Ko C Y, Lo Y K, Lu P J. The binding and phosphorylation of Thr231 is critical for Tau's hyperphosphorylation and functional regulation by glycogen synthase kinase 3B. J. Neurochem. 2007; 103: 802-813.

Lin et al., Ultrastructural neuronal pathology in transgenic mice expressing mutant (P301L) human tau. J Neurocytol. 2003; 32 (9): 1091-1105.

Liu, F., Grundke-Iqbal, I., Iqbal, K., and Gong, C. X. Contributions of protein phosphatases PP1, PP2A, PP2B and PP5 to the regulation of tau phosphorylation. Eur. J. Neurosci. 2005; 22:1942-1950.

Malakoutikhah M, Teixidó M, Giralt E. Shuttle-Mediated Drug Delivery to the Brain. Angew. Chem., Int. Ed., 2011, 50, 7998-8014.

Manfredini S, Pavan B, Vertuani S, Scaglianti M, Compagnone D, Biondi C, et al. Design, synthesis and activity of ascorbic acid prodrugs of nipecotic, kynurenic and diclophenamic acids, liable to increase neurotropic activity. J. Med. Chem., 2002, 45, 559-562.

Medina M, and Avila J. Further understanding of tau phosphorylation: implications for therapy. Expert Rev Neurother 2015; 15:115-22.

Nakagawa S. Deli M A, Kawaguchi H, Shimizudani T, Shimono T, Kittel A, Tanaka K, Niwa M. A new blood-brain barrier model using primary rat brain endothelial cells, pericytes and astrocytes. Neurochem. Int., 2009, 54, 253-263.

Nakamura et al., Immunohistochemical localization of Ca (2+)/calmodulin-dependent protein kinase kinase beta in the rat central nervous system. Neurosci Res 2001; 39:175-88.

Neddens, J., Temmel, M., Flunkert, S., Kerschbaumer, B., Hoeller, C., Loeffler, T. Hutter-Paier, B. Phosphorylation of different tau sites during progression of Alzheimer's disease. Acta Neuropathol Comm 2018; 6 (1): 52.

Ng S K. Generation of high-expressing cells by methotrexate amplification of destabilized dihydrofolate reductase selection marker. Methods Mol Biol. 2012; 801:161-72.

Patabendige A, Skinner R A, Morgan L, Abbott N J. A detailed method for preparation of a functional and flexible blood-brain barrier model using porcine brain endothelial cells. Brain research 2013; 1521:16-30.

Prades, R., Oller-Salvia, B., Schwarzmaier, S. M., Selva, J., Moros, M., Balbi, M., Grazú, V., de La Fuente, J. M., Egea, G., Plesnila, N., Teixidó, M., Giralt, E., Angew. Chem., Int. Ed., 2015, 54, 3967.

Reilly et al., Amyloid deposition in the hippocampus and entorhinal cortex: quantitative analysis of a transgenic mouse model. Proc Natl Acad Sci USA. 2003; 100:4837-42. Reiman E M. Alzheimer's disease: Attack on amyloid-β protein. Nature 2016 Sep. 1; 537:36.

Rub et al., The evolution of Alzheimer's disease-related cytoskeletal pathology in the human raphe nuclei. Neuropathol Appl Neurobiol 2000; 26:553-67.

Rosenmann H. Asparagine endopeptidase cleaves tau and promotes neurodegeneration. Nat Med2014; 20:1236-1238.

Sagare et al., A lipoprotein receptor cluster IV mutant preferentially binds amyloid-β and regulates its clearance from the mouse brain. J. Biol. Chem. 2013; 288:15154-15166.

Salminen et al., AMP-activated protein kinase: a potential player in Alzheimer's disease. J Neurochem 2011; 118: 460-74.

Sand K M, Bern M, Nilsen J, et al. Unraveling the interation between FcRn and albumin: opportunities for design of albumin-based therapeutics. Frontiers in Immunology, 2015, 5 (682), 1-21.

Sassin et al., Evolution of Alzheimer's disease-related cytoskeletal changes in the basal nucleus of Meynert. Acta Neuropathol 2000; 100:259-69.

Selenica M L, Wang X, Ostergaard-Pedersen L, Westlind-Danielsson A, Grubb A. Cystatin C reduces the in vitro formation of soluble Aβ1-42 oligomers and protofibrils. Scand J Clin Lab Invest. 2007; 67:179-190.

Sengupta, A. et al. Phosphorylation of tau at both Thr 231 and Ser 262 is required for maximal inhibition of its binding to microtubules. Arch. Biochem. Biophys. 1998; 357:299-309.

Seubert et al., Detection of phosphorylated Ser262 in fetal tau, adult tau, and paired helical filament tau. J Biol Chem 1995; 270:18917-22.

Sevigny et al. The antibody aducanumab reduces Aβ plaques in Alzheimer's disease. Nature 2016 Sep. 1; 537:50.

Spillantini M G, and Goedert M. Tau pathology and neurodegeneration. Lancet Neurol 2013; 12:609-22.

Steinberg G R, and Kemp B E. AMPK in Health and Disease. Physiol Rev 2009; 89:1025-78.

Su Y, and Ni B. Selective Deposition of Amyloid-b Protein in the Entorhinal-Dentate Projection of a Transgenic Mouse Model of Alzheimer's Disease. Journal of Neuroscience Research. 1998; 53:177-186.

Sundelof J, Arnlov J, Ingelsson E, Sundstrom J, Basu S, et al. Serum cystatin C and the risk of Alzheimer disease in elderly men. Neurology 2008; 71:1072-1079.

Tan et al., Bcl-X(L) inhibits apoptosis and necrosis produced by Alzheimer's beta-amyloid1-40 peptide in PC12 cells. Neuroscience Letters 1999; 272:5.

Thornton et al., AMP-activated protein kinase (AMPK) is a tau kinase, activated in response to amyloid b-peptide exposure. Biochem. J. 2011; 434, 503-512.

Tizon et al., Cystatin C protects neuronal cells from amyloid-beta-induced toxicity. J Alzheimers Dis 2010; 19 (3): 885-94.

Toschi et al. Activation of matrix-metalloproteinase-2 and membrane-type-1-matrix-metalloproteinase in endothelial cells and induction of vascular permeability in vivo by human immunodeficiency virus-1 Tat protein and basic fibroblast growth factor. Mol Biol Cell 2001; 12:2934-2946.

Trojanowski et al., Distribution of tau proteins in the normal human central and peripheral nervous system. J Histochem Cytochem. 1989; 37:209-215.

Tulving E, and Markowitsch H J. Episodic and declarative memory: role of the hippocampus. Hippocampus 1998; 8:198-204.

van Kasteren et al., A Multifunctional Protease Inhibitor to Regulate Endolysosomal Function, ACS Chem. Biol. 2011, 6, 1198-1204.

van Strien N M, Cappaert N L, Witter M P. The anatomy of memory: an interactive overview of the parahippocampal-hippocampal network. Nat Rev Neurosci. 2009; 10:272-282.

Vingtdeux et al., AMPK is abnormally activated in tangle- and pre-tangle-bearing neurons in Alzheimer's disease and other tauopathies. Acta Neuropathol. 2011 March; 121 (3): 337-49.

Vitale et al., Anti-tau conformational scFv MC1 antibody efficiently reduces pathological tau species in adult JNPL3 mice. Acta Neuropathol Commun. 2018; 6:82.

Walsh D M, and Teplow D B. Alzheimer's Disease and the Amyloid beta-Protein. Prog Mol Biol Transl Sci. 2012; 107:101-124.

Wang et al., Kinases and phosphatases and tau sites involved in Alzheimer neurofibrillary degeneration. Eur J Neurosci. 2007; 25:59-68.

Wang J Z, Xia Y Y, Grundke-Iqbal I, Iqbal K. Abnormal hyperphosphorylation of tau: sites, regulation, and molecular mechanism of neurofibrillary degeneration. J Alzheimers Dis 2013; 33 (Suppl 1): S123-139.

Wang N, Jin X, Zhu X. Construction of biomimetic long-circulation delivery platform encapsulated by zwitterionic polymers for enhanced penetration of blood-brain barrier. RSC Adv., 2017, 7, 20766-20778.

Xu et al., HIV-1 TAT protein increases the permeability of brain endothelial cells by both inhibiting occludin expression and cleaving occludin via matrix metalloproteinase-9. Brain Res. 2012; 1436:13-19

Xu W, Fitzgerald S, Nixon R A, Levy E, and Wilson D A. Early hyperactivity in lateral entorhinal cortex is associated with elevated levels of AβPP metabolites in the Tg2576 mouse model of Alzheimer's disease. Exp Neurol. 2015 February; 264:82-91.

Zhang et al., Peptides in cancer nanomedicine: drug carriers, targeting ligands and protease substrates. J Control Release 2012; 159:2-13.

Zhang et al., Tumor-suppressor PTEN affects tau phosphorylation, aggregation, and binding to microtubules. FASEB J 2006 June; 20 (8): 1272-4.

Zhao et al., Effects of PTEN inhibition on the regulation of Tau phosphorylation in rat cortical neuronal injury after oxygen and glucose deprivation. Brain Injury 2016, 30, 1150-1159

Zhong et al. (2012) HIV-1 TAT triggers nuclear localization of ZO-1 via Rho signaling and cAMP response element-binding protein activation. J. Neurosci. 32, 143-150.

Zong et al., Homodimerization Is Essential for the Receptor for Advanced Glycation End Products (RAGE)-mediated Signal Transduction. J. Biol. Chem. 2010, 285, 23137-23146.

All of the references cited herein are incorporated by reference in their entirety.

Those skilled in the art will recognize, or be able to ascertain using no more than routine experimentation, many equivalents to the specific embodiments of the invention specifically described herein.

We claim:

1. A method for decreasing both amyloid beta (Abeta) plaque deposition and hyperphosphorylated Tau plaque deposition in a brain in a subject suffering from Alzheimer's disease (AD) compared to the Abeta plaque deposition and hyperphosphorylated Tau plaque deposition in the brain of the subject suffering from AD with no treatment, comprising administering systemically to the subject suffering from AD, an effective amount of a recombinantly produced Cystatin C (CysC) fusion polypeptide comprising in N-terminus to C-terminus order, a full length wild type Cystatin C (CysC), a first linker, a Human Serum Albumin protein, a second linker, and a specific cell penetrating peptide, wherein the first linker is GGSAS (SEQ ID NO: 1) or GGGSGGGS (SEQ ID NO:2), the second linker is GFLG (SEQ ID NO:3), and the cell penetrating peptide consists of amino acid residues 715-737 of the amino acid sequence of SEQ ID NO:6; and wherein the effective amount is about 5 mg/kg or 10 mg/kg of body weight.

2. The method of claim 1, wherein the CysC fusion polypeptide consists of the amino acid sequence of SEQ ID NO:6.

3. A method for lowering both Abeta plaque and hyperphosphorylated Tau tangle plaque in a brain of a subject suffering from Alzheimer's disease (AD) compared to the Abeta plaque and hyperphosphorylated Tau tangle plaque in the brain of the subject suffering from AD with no treatment, comprising administering to the subject suffering from AD an isolated polypeptide consisting of the amino acid sequence of SEQ ID NO:6.

4. The method of claim 3, wherein the polypeptide is administered to the subject at a dose of about 1 to 10 mg/Kg of body weight.

\* \* \* \* \*